US008426674B2

(12) United States Patent
Kiyokawa et al.

(10) Patent No.: US 8,426,674 B2
(45) Date of Patent: Apr. 23, 2013

(54) METHOD FOR PRODUCTION OF TRACP5B

(75) Inventors: Iwao Kiyokawa, Fukushima (JP);
Tatsuya Ohashi, Fukushima (JP);
Toshihide Miura, Fukushima (JP);
Katsuhiro Katayama, Fukushima (JP);
Toshiki Tamura, Ibaraki (JP); Isao Kobayashi, Ibaraki (JP); Hideki Sezutsu, Ibaraki (JP)

(73) Assignees: Nitto Boseki Co., Ltd., Fukushima (JP);
National Institute of Agrobiological Sciences, Ibaraki (JP)

( * ) Notice: Subject to any disclaimer, the term of this patent is extended or adjusted under 35 U.S.C. 154(b) by 275 days.

(21) Appl. No.: 12/521,701

(22) PCT Filed: Dec. 28, 2007

(86) PCT No.: PCT/JP2007/075263
§ 371 (c)(1),
(2), (4) Date: Feb. 16, 2010

(87) PCT Pub. No.: WO2008/081922
PCT Pub. Date: Jul. 10, 2008

(65) Prior Publication Data
US 2011/0239313 A1    Sep. 29, 2011

(30) Foreign Application Priority Data
Dec. 28, 2006 (JP) .................................. 2006-353542

(51) Int. Cl.
*A01K 67/04* (2006.01)
(52) U.S. Cl.
USPC .................................... 800/13; 800/4; 800/21
(58) Field of Classification Search .................... 800/13, 800/4, 21
See application file for complete search history.

(56) References Cited

U.S. PATENT DOCUMENTS

| 7,074,903 | B2 | 7/2006 | Ohashi et al. |
| 7,459,599 | B2 * | 12/2008 | Tamura et al. ..................... 800/4 |
| 7,465,556 | B2 | 12/2008 | Miura et al. |
| 2005/0177877 | A1 | 8/2005 | Hiramatsu et al. |
| 2006/0070132 | A1 | 3/2006 | Tamura et al. |
| 2006/0115866 | A1 | 6/2006 | Ohashi |
| 2008/0301823 | A1 | 12/2008 | Tomita et al. |
| 2011/0021757 | A1 | 1/2011 | Tamura |

FOREIGN PATENT DOCUMENTS

| EP | 1 947 180 A1 | 7/2008 |
| JP | 2004-026805 A | 1/2004 |
| JP | 2004-135528 A | 5/2004 |
| JP | 2005/095063 | 4/2005 |
| JP | 2006/109772 | 4/2006 |
| JP | 2006/137739 | 6/2006 |
| WO | 03/074699 | 9/2003 |
| WO | 2004/059320 A1 | 7/2004 |
| WO | 2004/077059 A1 | 9/2004 |
| WO | 2007/046439 A1 | 4/2007 |

OTHER PUBLICATIONS

Imamura et al. (2003) Genetics, vol. 165, 1329-1340.*
Ljusberg et al. (2005) J. Biol. Chem., vol. 280(31), 28370-28381.*
Tomita et al. (2003) Nat. Biotech., vol. 21, 52-56.*
Imamura et al., "Targeted Gene Expression Using the GAL4/UAS System in the Silkworm *Bombyx mori*," Genetics 165:1329-40 (2003).
International Preliminary Report on Patentability and Written Opinion of the International Searching Authority for International Patent Application No. PCT/JP2007/075263 (Jul. 16, 2009).
Ljusberg et al., "Proteolytic Excision of a Repressive Loop Domain in Tartrate-resistant Acid Phosphatase by Cathepsin K in Osteoclasts," The Journal of Biological Chemistry 280(31):28370-81 (2005).
Igarashi et al., "Heparin Column Analysis of Serum Type 5 Tartrate-resistant Acid Phosphatase Isoforms," Journal of Chromatography B 757:269-276 (2001).
Supplementary European Search Report for EP 07 86 0466 dated Oct. 15, 2010.
Hayman et al., "Purple Acid Phosphatase of the Human Macrophage and Osteoclast," The Journal of Biological Chemistry 269(2):1294-1300 (1994).
Lam et al., "Biochemical Properties of Tartrate-Resistant Acid Phosphatase in Serum of Adults and Children," Clinical Chemistry 24(7):1105-8 (1978).
Stepan et al., "Purification and N-Terminal Amino Acid Sequence of the Tartrate-Resistant Acid Phosphatase from Human Osteoclastoma: Evidence for a Single Structure," Biochemical and Biophysical Research Communications 168(2):792-800 (1990).
Abstract of the 27th Annual Meeting of the Molecular Biology Society of Japan; 3PB-533, 3PB-534 (2004). "Development of a transgenic silkworm expression system in which recombinant proteins can be extracted from cocoons without using protein denaturants." English translation.
Knowledge Cluster Initiative, Hiroshima Bio Cluster, Result Report 2004. "Development of a recombinant human collagen production system." English translation.
Abstract of the 76th meeting of the Japanese Society of Sericultural Science, p. 31, 128 (2006). "Development of a silkworm enhancer trap system: development of a gene expression regulatory system (Tet-OFF) using tetracycline." English translation.
Abstract of the 78th Annual Meeting of the Genetics Society of Japan 2E04 (2006). "Development of a silkworm enhancer trap system: development of a gene expression regulatory system (tetOOFF) using tetracycline." English translation.

* cited by examiner

*Primary Examiner* — Anne Marie S Wehbe
(74) *Attorney, Agent, or Firm* — David S. Resnick; Mark J. FitzGerald; Nixon Peabody LLP

(57) ABSTRACT

Silkworms which have (i) a DNA encoding a transcriptional regulator operably linked downstream of a promoter of a DNA encoding a protein specifically expressed in the silk gland and (ii) a DNA encoding TRACP5 operably linked downstream of a target promoter of the transcriptional regulator were produced. The result showed that active TRACP5b was produced from the silkworms. This means that TRACP5 produced from the silk gland of the silkworms undergoes processing in the silk gland that is similar to the processing taking place at bone resorption sites.

22 Claims, 5 Drawing Sheets

SEQUENCE LISTING

```
<160> NUMBER OF SEQ ID NOS: 10

<210> SEQ ID NO 1
<211> LENGTH: 7330
<212> TYPE: DNA
<213> ORGANISM: Artificial
<220> FEATURE:
<223> OTHER INFORMATION: An artificially synthesized nucleotide sequence

<400> SEQUENCE: 1
gacgaaaggg cctcgtgata cgcctatttt tataggttaa tgtcatgata ataatggttt      60
```

-continued

| | |
|---|---|
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca aacaaaaaaa ccaccgctac cagcggtggt ttgtttgccg gatcaagagc | 1320 |
| taccaactct ttttccgaag gtaactggct tcagcagagc gcagatacca aatactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg tcgggctga acggggggtt | 1560 |
| cgtgcacaca gcccagcttg gagcgaacga cctacaccga actgagatac ctacagcgtg | 1620 |
| agcattgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg attttttgtga tgctcgtcag | 1800 |
| ggggggcggag cctatggaaa aacgccagca acgcggcctt tttacggttc ctggccttt | 1860 |
| gctggccttt tgctcacatg ttcttttcctg cgttatcccc tgattctgtg ataaccgta | 1920 |
| ttaccgcctt tgagtgagct gataccgctc gccgcagccg aacgaccgag cgcagcgagt | 1980 |
| cagtgagcga ggaagcggaa gagcgcccaa tacgcaaacc gcctctcccc gcgcgttggc | 2040 |
| cgattcatta atgcagctgg cacgacaggt ttcccgactg gaaagcgggc agtgagcgca | 2100 |
| acgcaattaa tgtgagttag ctcactcatt aggcacccca ggctttacac tttatgcttc | 2160 |
| cggctcgtat gttgtgtgga attgtgagcg ataacaatt tcacacagga aacagctatg | 2220 |
| accatgatta cgaattgatc ctctagctag agtcgacgct cgcgcgactt ggtttgccat | 2280 |
| tctttagcgc gcgtcgcgtc acacagcttg gccacaatgt ggttttttgtc aaacgaagat | 2340 |
| tctatgacgt gtttaaagtt taggtcgagt aaagcgcaaa tctttttttaa ccctagaaag | 2400 |
| atagtctgcg taaaattgac gcatgcattc ttgaaatatt gctctctctt tctaaatagc | 2460 |

```
gcgaatccgt cgctgtgcat ttaggacatc tcagtcgccg cttggagctc ccgtgaggcg    2520
tgcttgtcaa tgcggtaagt gtcactgatt ttgaactata acgaccgcgt gagtcaaaat    2580
gacgcatgat tatctttac gtgacttta agatttaact catacgataa ttatattgtt    2640
atttcatgtt ctacttacgt gataacttat tatatatata ttttcttgtt atagatatca    2700
agcttatcga taccgtcgac ctcgaccgct agtgccgagt ctctgcactg aacattgtca    2760
gatctcgagc tcaagcttgc atgcctgcag gtcggagtac tgtcctccga gcggagtact    2820
gtcctccgag cggagtactg tcctccgagc ggagtactgt cctccgagcg gagtactgtc    2880
ctccgagcgg agactctagc gagcgccgga gtataaatag aggcgcttcg tctacggagc    2940
gacaattcaa ttcaaacaag caaagtgaac acgtcgctaa gcgaaagcta agcaaataaa    3000
caagcgcagc tgaacaagct aaacaatctg cagtaaagtg caagttaaag tgaatcaatt    3060
aaaagtaacc agcaaccaag taaatcaact gcaactactg aaatctgcca agaagtaatt    3120
attgaataca agaagagaac tctgaatagg gaattggcct agtagaccta aatgaaatt    3180 cttagtcaac gttgcccttg tttttatggt cgtatacatt tcttacatct atgccggcat    3240
gcatatggcc acccctgccc tgcgctttgt agccgtgggt gactggggag gggtccccaa    3300
tgccccattc cacacggccc gggaaatggc caatgccaag gagatcgctc ggactgtgca    3360
gatcctgggt gcagacttca tcctgtctct aggggacaat ttttacttca ctggtgtgca    3420
agacatcaat gacaagaggt tccaggagac ctttgaggac gtattctctg accgctccct    3480
tcgcaaagtg ccctggtacg tgctagccgg aaaccatgac caccttggca atgtctctgc    3540
ccagattgca tactctaaga tctccaagcg ctggaacttc cccagccctt tctaccgcct    3600
gcacttcaag atcccacaga ccaatgtgtc tgtggccatt tttatgctgg acacagtgac    3660
actatgtggc aactcagatg acttcctcag ccagcagcct gagaggcccc gagacgtgaa    3720
gctggcccgc acacagctgt cctggctcaa gaaacagctg gcggcggcca gggaggacta    3780
cgtgctggtg gctggccact accccgtgtg gtccatagcc gagcacgggc ctacccactg    3840
cctggtcaag cagctacggc cactgctggc cacatacggg gtcactgcct acctgtgcgg    3900
ccacgatcac aatctgcagt acctgcaaga tgagaatggc gtgggctacg tgctgagtgg    3960
ggctgggaat tcatggacc cctcaaagcg gcaccagcgc aaggtcccca acggctatct    4020
gcgcttccac tatgggactg aagactcact gggtggcttt gcctatgtgg agatcagctc    4080
caaagagatg actgtcactt acatcgaggc ctcgggcaag tccctctta agaccaggct    4140 gccgaggcga gccaggccct aatctaggtc agccataccaa catttgtaga ggttttactt    4200
gctttaaaaa acctcccaca cctcccctg aacctgaaac ataaaatgaa tgcaattgtt    4260
gttgttaact tgtttattgc agcttataat ggttacaaat aaagcaatag catcacaat    4320 ttcacaaata aagcatttt ttcactgcat tctagttgtg gtttgtccaa actcatcaat    4380
gtatcttaag gcgtaaattg taagcgttaa tattttgtta aaattcgcgt taaattttg    4440 ttaaatcagc tcattttta accaataggc cgaaatcggc aaaatccctt ataaatcaaa    4500
agaatagacc gagatagggt tgagtgttgt tccagttgg aacaagagtc cactattaaa    4560
gaacgtggac tccaacgtca aagggcacta gcggtcgagc tcaagcttgc atgcctgcag    4620
gaattctgag tttggacaaa ccacaactag aatgcagtga aaaaaatgct ttatttgtga    4680
aatttgtgat gctattgctt tatttgtaac cattataagc tgcaataac aagttaacaa    4740 caacaattgc attcatttta tgtttcaggt tcaggggag gtgtgggagg ttttttaaag    4800
caagtaaaac ctctacaaat gtggtatggc tgattatgat ctagagtcgc ggccgcttta    4860
```

```
cttgtacagc tcgtccatgc cgagagtgat cccggcggcg gtcacgaact ccagcaggac   4920
catgtgatcg cgcttctcgt tggggtcttt gctcagggcg gactgggtgc tcaggtagtg   4980
gttgtcgggc agcagcacgg ggccgtcgcc gatggggtg ttctgctggt agtggtcggc    5040
gagctgcacg ctgccgtcct cgatgttgtg gcggatcttg aagttcacct tgatgccgtt   5100
cttctgcttg tcggccatga tatagacgtt gtggctgttg tagttgtact ccagcttgtg   5160
ccccaggatg ttgccgtcct ccttgaagtc gatgccttc agctcgatgc ggttcaccag    5220
ggtgtcgccc tcgaacttca cctcggcgcg ggtcttgtag ttgccgtcgt ccttgaagaa   5280
gatggtgcgc tcctggacgt agccttcggg catggcggac ttgaagaagt cgtgctgctt   5340
catgtggtcg gggtagcggc tgaagcactg cacgccgtag gtcagggtgg tcacgagggt   5400
gggccagggc acgggcagct tgccggtggt gcagatgaac ttcagggtca gcttgccgta   5460
ggtggcatcg ccctcgccct cgccggacac gctgaacttg tggccgttta cgtcgccgtc   5520
cagctcgacc aggatgggca ccaccccggt gaacagctcc tcgcccttgc tcaccatggt   5580
ggcgaccggt ggatcccggg cccgcggtac cgtcgactct agcggtaccc cgattgttta   5640
gcttgttcag ctgcgcttgt ttatttgctt agctttcgct tagcgacgtg ttcactttgc   5700
ttgtttgaat tgaattgtcg ctccgtagac gaagcgcctc tatttatact ccggcggtcg   5760
agggttcgaa atcgataagc ttggatccta attgaattag ctctaattga attagtctct   5820
aattgaatta gatccccggg cgagctcgaa ttaaccattg tgggaaccgt gcgatcaaac   5880
aaacgcgaga taccggaagt actgaaaaac agtcgctcca ggccagtggg aacatcgatg   5940
ttttgttttg acggaccccct tactctcgtc tcatataaac cgaagcgaat tcgatggcgc   6000
gccataaaag ttttgttact ttatagaaga aattttgagt ttttgttttt ttttaataaa   6060
taaataaaca taaataaatt gtttgttgaa tttattatta gtatgtaagt gtaaatataa   6120
taaaacttaa tatctattca aattaataaa taaacctcga tatacagacc gataaaacac   6180
atgcgtcaat tttacgcatg attatcttta acgtacgtca caatatgatt atctttctag   6240
ggttaaataa tagtttctaa tttttttatt attcagcctg ctgtcgtgaa taccgtatat   6300
ctcaacgctg tctgtgagat tgtcgtattc tagccttttt agttttttcgc tcatcgactt   6360 gatattgtcc gacacatttt cgtcgatttg cgttttgatc aaagacttga gcagagacac   6420
gttaatcaac tgttcaaatt gatccatatt aacgatatca acccgatgcg tatatggtgc   6480
gtaaaatata tttttaacc ctcttatact ttgcactctg cgttaatacg cgttcgtgta    6540
cagacgtaat catgtttttct tttttggata aaactcctac tgagtttgac ctcatatattag 6600 accctcacaa gttgcaaaac gtggcatttt ttaccaatga agaatttaaa gttatttaa    6660 aaaatttcat cacagattta agaagaacc aaaaattaaa ttatttaatc gaccagttaa    6720
tcaacgtgta cactgacgcg tcggcaaaaa acacgcagcc cgacgtgttg gctaaaatta   6780
ttaaatcaac ttgtgttata gtcacggatt tgccgtccaa cgtgttcctc aaaaagttga   6840
agaccaacaa gtttacggac actattaatt atttgatttt gccccacttc attttgtggg   6900
atcacaattt tgttatattt taaacaaagc ttggcactgg ccgtcgtttt acaacgtcgt   6960
gactgggaaa accctggcgt tacccaactt aatcgccttg cagcacatcc cccttcgcc    7020 agctggcgta atagcgaaga ggcccgcacc gatcgccctt cccaacagtt gcgcagcctg   7080
aatggcgaat ggcgcctgat gcggtatttt ctccttacgc atctgtgcgg tatttcacac   7140
cgcatatggt gcactctcag tacaatctgc tctgatgccg catagttaag ccagccccga   7200
cacccgccaa cacccgctga cgcgccctga cgggcttgtc tgctcccggc atccgcttac   7260
```

-continued

```
agacaagctg tgaccgtctc cgggagctgc atgtgtcaga ggttttcacc gtcatcaccg    7320
aaacgcgcga                                                            7330
```

<210> SEQ ID NO 2
<211> LENGTH: 20
<212> TYPE: DNA
<213> ORGANISM: Artificial
<220> FEATURE:
<223> OTHER INFORMATION: An artificially synthesized nucleotide sequence

<400> SEQUENCE: 2

```
gggtgcagac ttcatcctgt                                                  20
```

<210> SEQ ID NO 3
<211> LENGTH: 20
<212> TYPE: DNA
<213> ORGANISM: Artificial
<220> FEATURE:
<223> OTHER INFORMATION: An artificially synthesized nucleotide sequence

<400> SEQUENCE: 3

```
gtttcttgag ccaggacagc                                                  20
```

<210> SEQ ID NO 4
<211> LENGTH: 978
<212> TYPE: DNA
<213> ORGANISM: Homo sapiens

<400> SEQUENCE: 4

```
atggacatgt ggacggcgct gctcatcctg caagccttgt tgctaccctc cctggctgat     60
ggtgccaccc ctgccctgcg ctttgtagcc gtgggtgact ggggaggggt ccccaatgcc    120
ccattccaca cggcccggga atggccaat gccaaggaga tcgctcggac tgtgcagatc    180
ctgggtgcag acttcatcct gtctctaggg gacaattttt acttcactgg tgtgcaagac   240
atcaatgaca agaggttcca ggagaccttt gaggacgtat tctctgaccg ctcccttcgc   300
aaagtgccct ggtacgtgct agccggaaac catgaccacc ttggcaatgt ctctgcccag   360
attgcatact ctaagatctc caagcgctgg aacttcccca gcccttccta ccgcctgcac   420
ttcaagatcc cacagaccaa tgtgtctgtg gccattttta tgctggacac agtgacacta   480
tgtggcaact cagatgactt cctcagccag cagcctgaga ggccccgaga cgtgaagctg   540
gcccgcacac agctgtcctg gctcaagaaa cagctggcgg cggccaggga ggactacgtg   600
ctggtggctg ccactaccc cgtgtggtcc atagccgagc acgggcctac ccactgcctg   660
gtcaagcagc tacggccact gctggccaca tacgggtca ctgcctacct gtgcggccac   720
gatcacaatc tgcagtacct gcaagatgag aatggcgtgg gctacgtgct gagtgggggct   780
gggaatttca tggacccctc aaagcggcac cagcgcaagg tccccaacgg ctatctgcgc   840
ttccactatg ggactgaaga ctcactgggt ggctttgcct atgtggagat cagctccaaa   900
gagatgactg tcacttacat cgaggcctcg ggcaagtccc tctttaagac caggctgccg   960
aggcgagcca ggccctga                                                  978
```

<210> SEQ ID NO 5
<211> LENGTH: 325
<212> TYPE: PRT
<213> ORGANISM: Homo sapiens

<400> SEQUENCE: 5

```
Met Asp Met Trp Thr Ala Leu Leu Ile Leu Gln Ala Leu Leu Leu Pro
 1               5                  10                  15
```

```
Ser Leu Ala Asp Gly Ala Thr Pro Ala Leu Arg Phe Val Ala Val Gly
            20                  25                  30

Asp Trp Gly Gly Val Pro Asn Ala Pro Phe His Thr Ala Arg Glu Met
        35                  40                  45

Ala Asn Ala Lys Glu Ile Ala Arg Thr Val Gln Ile Leu Gly Ala Asp
    50                  55                  60

Phe Ile Leu Ser Leu Gly Asp Asn Phe Tyr Phe Thr Gly Val Gln Asp
65                  70                  75                  80

Ile Asn Asp Lys Arg Phe Gln Glu Thr Phe Glu Asp Val Phe Ser Asp
                85                  90                  95

Arg Ser Leu Arg Lys Val Pro Trp Tyr Val Leu Ala Gly Asn His Asp
            100                 105                 110

His Leu Gly Asn Val Ser Ala Gln Ile Ala Tyr Ser Lys Ile Ser Lys
        115                 120                 125

Arg Trp Asn Phe Pro Ser Pro Phe Tyr Arg Leu His Phe Lys Ile Pro
    130                 135                 140

Gln Thr Asn Val Ser Val Ala Ile Phe Met Leu Asp Thr Val Thr Leu
145                 150                 155                 160

Cys Gly Asn Ser Asp Asp Phe Leu Ser Gln Gln Pro Glu Arg Pro Arg
                165                 170                 175

Asp Val Lys Leu Ala Arg Thr Gln Leu Ser Trp Leu Lys Lys Gln Leu
            180                 185                 190

Ala Ala Ala Arg Glu Asp Tyr Val Leu Val Ala Gly His Tyr Pro Val
        195                 200                 205

Trp Ser Ile Ala Glu His Gly Pro Thr His Cys Leu Val Lys Gln Leu
    210                 215                 220

Arg Pro Leu Leu Ala Thr Tyr Gly Val Thr Ala Tyr Leu Cys Gly His
225                 230                 235                 240

Asp His Asn Leu Gln Tyr Leu Gln Asp Glu Asn Gly Val Gly Tyr Val
                245                 250                 255

Leu Ser Gly Ala Gly Asn Phe Met Asp Pro Ser Lys Arg His Gln Arg
            260                 265                 270

Lys Val Pro Asn Gly Tyr Leu Arg Phe His Tyr Gly Thr Glu Asp Ser
        275                 280                 285

Leu Gly Gly Phe Ala Tyr Val Glu Ile Ser Ser Lys Glu Met Thr Val
    290                 295                 300

Thr Tyr Ile Glu Ala Ser Gly Lys Ser Leu Phe Lys Thr Arg Leu Pro
305                 310                 315                 320

Arg Arg Ala Arg Pro
            325

<210> SEQ ID NO 6
<211> LENGTH: 21
<212> TYPE: PRT
<213> ORGANISM: Homo sapiens

<400> SEQUENCE: 6

Met Asp Met Trp Thr Ala Leu Leu Ile Leu Gln Ala Leu Leu Leu Pro
1               5                   10                  15

Ser Leu Ala Asp Gly
            20

<210> SEQ ID NO 7
<211> LENGTH: 1935
<212> TYPE: DNA
<213> ORGANISM: Bombyx mori
```

<400> SEQUENCE: 7

```
gaaattctta gctacatcta gcccagactg taagagtttc ttaggagctt tagaagttaa    60
agaagtacct ttgtgttgct gatccttcta tatcatctgg tcctagtaaa ggtactctct   120
tataatctcc ttcctaattc cttacctgct atttatcgat tgtaggtcgt cttggaaacc   180
agtaccactg tacaaactcg cgccccatta gtaacgtgat ttgaacggcc aaccaattga   240
tgttttaatg caattaatat cgtatcttta accccaacgt ggttctgcgt taactaagtg   300
ctcaccgctg tcaacagcaa taaaaccatt tttgaaataa taacatcatt acactaacat   360
agtgagctag tcgcaaaatg tatgtagaga gaaaacaaac cttctttggg gtgttgagag   420
gaaatcgctg gattagaact atcgtgaaga ccattcactg atcctgtgta cttaaattcg   480
cggattcagc attaagcgcc ggatctcagt tccatcgtaa tcccagttaa agaggtgaaa   540
ttagctatca cttcgatatc tgttctgaaa gcaatgttcc acttgtaaaa gcataagcgg   600
tcagaaacct tgttaaccaa tagagccaaa tatagttaac acaatagaaa tttatccaaa   660
tattattcgt gtattgttta tagcctttgt caagtctttt acaaggcaag ataataagta   720
atattccgtg attggacgta acatttcccg gaagatcctt agccgataag tcgaagagcc   780
gcatgtggct agagagacgc gggtttccga ccactggctt aggcgcttat tccgccataa   840
tagatgtacg tgttcacaat tagcacccga aattcgtaat agctacgaga agtatcgaat   900
atcaaaaatc tatatattaa tacgtgaagc aaaaactttg tatccctttt tacgaaaatt   960
gcgaggacgg aggagtatga aatttcccac acttatagag aatacagaga agaagtgcac  1020
aatgctaata tttttttaaa ataatgcata aagatactt taaatcaata agaaaacag   1080
cacacacact ataccatg tatttgacgc acacacgcat gtatactatt tattgtcaaa   1140
cttttgttct tgacgtctgt gttcaaactg agaatagatt aaatattgtt tgtctttatt  1200
aatatttttt aatagtgtag tcttggcgaa atttgtgatt atagaagtat aaaatacaat  1260
cataatagtg tacaaactta caattcccaa ttaattatag tcgaatttcg actactgcgg  1320
gacctctagt attaataatt ctctttaaaa aaaaacagag catcaaatac tgtcacaaat  1380
gtcaagcggg tctcaacgag ccatgaataa attagaaatc aattaataac ataaaatagg  1440
caaacaaaat aaaaccattt acatagagaa cgtttgttga acaaaaacaa taacttgtat  1500
acattgtttg cacaaatgtt tgaaccgaaa atttattact ctctacgtaa gcttgatcaa  1560
acttcgtttt cgtataaaac gcgttggccc aaccactttg gcatagtcgt cttatcatcg  1620
ggtctctaag gatcaagcga tccaaagacc gccaacatgc gtttcgttct gtgctgcact  1680
ttgattgcgt tggctgtgag tatcattgct tcgttatcaa caatgacgta tttactaaga  1740
acactcttag atatgccttc aaattaaagc tttcaaagct ctgaagttca ccaaatgcga  1800
ctgttttagc gtaagcattt ctatccccca acagccattt agcgactacc cgaaaatcac  1860
tcgatttaac ttgggagttt ctgcaattta aaagttcaca ggtcgtctcc gattatactt  1920
ttaaacgctt cgcgc                                                   1935
```

<210> SEQ ID NO 8
<211> LENGTH: 2036
<212> TYPE: DNA
<213> ORGANISM: Bombyx mori

<400> SEQUENCE: 8

```
cagaatctac cacgatcgga aacgcgaccc actgagaaga tccggcgaga aactcagtga    60
gctgtgtcta tgggttaatt tactcgtcga gccctgttta ctgtttaggg cgacgtcgac   120
```

```
tgttaccatt cggtctacag gatcgagtgt gcattcttgt atcatcgttc tattatcacg    180
agtcattttg cgttttttcg gatccctgg aagtcgtcgt ggcctaagag ataagaagtc    240
cggtgcattc gtgttgagcg atgcacctgt gttcgaatcc taggcgggta ccaattttc    300 taatgaatta cgtacccaac aaatgttcac gattgccttc cacggtgaag gaataacatc    360
gtgcaataaa agtgaaaccc gcaaaatccg gtgcttttaa gcttttcaag caccggtcac    420
catcctcgtt gaactcatcg atctacaagc gatctaatct atagacccaa tccactaaga    480
tctcaccgga tcttctcagt ggttcgcatt ccagtggtag attcaattcg ctgctcttgc    540
tagggctagt gttagcaaat tccttcgggt taagcccgag agctcaccta ccgtccgcg    600 ctaagctgga aaagccctt aagctgtttt tttttgtat agcctttatt gctaatacta    660
aacaataact aataatttta catacagtaa caaattgttt taacttaaat ctaatacatc    720
ggatttcccg gttcagtgat cagcgtgtcc tgtgacacat aggcctcttc cagctgcttt    780 cattttctc tattggtagc ttttcttgac cagattgtct ctccaatcat cttgatatcg    840
tctgtccatc ttctagcttg cctggctctt ttcctttaaa ccaggggtcg tgaattcaat    900
cctcacagga agccgggatt aggtgggaga atatagttcc gatgttttga atgctttata    960
ttttctgtgg tcgaaaatga tactagagct acgcgtcgac aattgaatat tatgctaact   1020
accctctatt tattaaaaga cttttacgat tcatttcgca cagaaccaat cgactggtt   1080 tagaggttta gcagtttgtt aatgaactc gttttcatct tcacgattag aggatcccag   1140
gtgttaggta aaggatattc tagattgcag gagattttc ataaataatc acgcgatgga   1200
gcggtaatca gccaacatag tcgatcggca tcattattgg agaccaaaca acacttcagt   1260
tatccaagcg cgtcttaagt cgcattcgga taatcttgaa tagcctggaa gtgaattttt   1320
aaaaagtttg tctcgaacaa acatcaatta ctttgtaatt gaaccgaaaa agaggataa   1380 acattattag cattcgttgt aatgaaatat aatgttgaca cagtttgacc gacgtgcact   1440
gtcttttgtg gcaccggcta tataaaggtg gtctgtccgt tctgagccac acgagtcatc   1500
atgaagatcc catacgtctt gctgttcctt gtggtgagtt gctttcgttt ttgatatgct   1560
ggttcctcag gagtctgtac taatgcttct gttttttattg tataaatgtg agcacttcac   1620
ggcctacgta accagctggt tacaatcacc gtccacgccg aaaaaatgag gcctgtatct   1680
aaattgtaac ataatttttg cacatttgat tctcatccca cgatttatt tatctttcat   1740 tcattttac tggtggtagg acgtcttgtg agtccgcacg tgcaccacct cacctatttc   1800
agccgtgaag cagtaatgcg cttcggtttg aagggtgggg cagccgttgt actttataaa   1860
cggagacctt agaactcatg tcccgagatg ggtggcagca tttacgttgc agatgtctat   1920
gggctccggt aaccacttaa cattttttt ttttcttttt tttttttttt tatcacgcta   1980
cgttaattgg tcccgtgata agttcgtaaa gaacttgtgt tacaggtacc agataa       2036
```

<210> SEQ ID NO 9
<211> LENGTH: 1027
<212> TYPE: DNA
<213> ORGANISM: Bombyx mori

<400> SEQUENCE: 9

```
gaattcaaat aacaaagtgg tgcctatccc acttttttg atccagacaa agaaaataag     60
tgttttcggt gagctgaaaa attaatttca ggaaacaaca aaaataatga cgcaaaagta    120
caccggagtg aaaataaaca ctaagaaagt aatcgctaaa aattattcat ctcgtgaatt    180
gattgagcgc gataataacg cagtactatt ggagagattc tatgtttaat atattaatga    240
```

```
tatgatataa aaaagggtgc gtgtacttat gtacgcgcgt aagaagttat actttatttt    300
cattaaattt atttctttt tttttatttca atttaatca atttgaaaaa aaatcgaata     360
aacaacatcc tcaaacatgc atattggaca tcccttttct tgacatcgta taaattcggt    420
aattctcggt acggttcgta aagttcacct gcggctatat tccgactcgc caagttacgt    480
cagtcgtatt gtaatgagcg atttagtggg caacttcatt ctgttaattt tgtgtcacgg    540
tgcgcgcgca tcgtaaaact tcactctcat agattttca taacgcgcct aaagaagtat     600
aacttcaata atttaaattt aaaaaaaaac atgcatagaa taattatatg aattatttaa    660
aatgtcattt accgacattg acataacaga cgacgttaac actacaaaac attttaattc    720
cacattgtta catattcaac agttaaattt gcgttaattc tcgatgcgaa caaatataag    780
aacaatcgga tcaattagat cgctttgttt cgaacaacac ttagtttaac tagaggcgta    840
cacctcaaga aatcatcttc attagaaact aaaccttaaa atcgcaataa taaagcatag    900
tcaattttaa ctgaaatgca aagtcttttg aacgttagat gctgtcagcg ttcgttggta    960
cagttgtttg atatttattt taattgtctt tttatatata aatagtggaa cattaatcac    1020
ggaatcc                                                               1027

<210> SEQ ID NO 10
<211> LENGTH: 51
<212> TYPE: DNA
<213> ORGANISM: Mus musculus

<400> SEQUENCE: 10
atggatttac aggtgcagat tatcagcttc ctgctaatca ttgtcacagt c              51
```

METHOD FOR PRODUCTION OF TRACP5B

This application is a U.S. national stage entry under 35 U.S.C. §371 of International Patent Application No. PCT/JP2007/075263, filed Dec. 28, 2007, which claims priority of Japanese Patent Application No. 2006-353542, filed Dec. 28, 2006.

TECHNICAL FIELD

The present invention relates to methods for producing tartrate-resistant acid phosphatase 5b (TRACP5b) using silkworms. The present invention also relates to silkworms that produce TRACP5b.

BACKGROUND ART

Acid phosphatases in serum can be separated by polyacrylamide gel electrophoresis into six bands, bands 0 to 5, from the starting point. Of these bands, band 5 shows resistance to tartrate, and is called band 5 tartrate-resistant acid phosphatase (TRACP5: tartrate-resistant acid phosphatase 5).

Band 5 is further separated into two bands by acidic disc electrophoresis, called TRACP5a and TRACP5b, respectively. TRACP5a is an enzyme originating from platelets and other components, and its blood level does not change. On the other hand, TRACP5b is considered to derive from osteoclasts, since its blood level changes with bone resorption. TRACP5b is needed in large amounts to screen for candidate compounds in developing TRACP5b-specific inhibitors, activators, or modulators.

Therefore, to date, many researchers have attempted to produce useful human TRACP5b. However, there are no successful examples of expressing TRACP5b directly in vivo, and it had to be purified from large amounts of osteoclastoma (Non-patent Document 1), or isolated from large amounts of fresh serum (Non-patent Document 2). Meanwhile, attempts to produce TRACP5b by expressing TRACP5 in insect cells (Non-patent Document 3) and allowing protease to act on the obtained TRACP5 in vitro, are known. However, the fact is that only a small amount of the desired substance can be obtained (Non-patent Document 4).

Previously, the present inventors have made attempts to produce TRACP5b by conducting various modifications on *Escherichia coli*, insect cells, mammalian cells, and such, but they were unsuccessful. The reason for this was that the special post-translational modification (Non-patent Document 4) during the production of TRACP5b cannot be reproduced in these systems. The present inventors also produced TRACP5 and then treated it with enzymes such as cathepsin K in vitro, but failed to establish a production method for an enzyme protein that is stable from the viewpoint of industrialization.

In recent years, techniques for producing gene products using silkworms have been developed, and research on methods for introducing foreign genes and regulating the expression of transgenes has progressed. They are expected to become novel methods for protein production. For example, it is known that recombinant proteins are produced by expressing transgenes in the silk gland using transgenic silkworm production technology. Since silkworms are eukaryotic organisms, they can produce proteins close to mammalian types, as compared to plants or microorganisms such as *E. coli*. In addition, since silkworms have silk glands, which are organs suitable for producing recombinant proteins, they are capable of producing almost 1 g of protein per animal. Furthermore, silkworms can be reared under clean conditions using an artificial diet, and large-scale rearing at the level of several tens of thousands of silkworms can be easily carried out. In addition, by carrying out the large-scale rearing of silkworms using mulberry leaves abundant in nature, large amounts of recombinant proteins can be obtained at a low cost.

Meanwhile, there are several known methods for producing virus-infected silkworm larvae using recombinant baculoviruses, and obtaining useful proteins such as interferons which are used for pharmaceuticals (antitumor/antiviral agents or such) and the like, from their body fluid. It can be said that these methods have also provided novel protein production methods that utilize the ability of silkworms to produce proteins.

[Non-patent Document 1] J. J. Stepan, K. H. W. Lau, S. Mohan, F. R. Singer, D. J. Baylink, (1990) Purification and N-Terminal Acid Sequence of the Tartrate-Resistant Acid Phosphatase from Human Osteoclastoma Evidence for a Single Structure. Biochemical and Biophysical Research Communications 168, 792-800.

[Non-patent Document 2] K. W. Lam, D. Ted Eastlund, Chin-Yang Li, Lung T. Yam, (1978) Biochemical Properties of Tartrate-Resistant Acid Phosphatase in Serum of Adults and Children Clinical Chemistry 24, 1105-1108.

[Non-patent Document 3] Alison R. Hayman, Timotyh M. Cox, (1994) Purple Acid Phosphatase of the Human Macrophage and Osteoclast. The Journal of Biological Chemistry 269, 1294-1300.

[Non-patent Document 4] Jenny Ljusberg, Yunling Wang, Pernilla Lang, Maria Norgard, Robert Dodds, Kjell Hultenby, Barbro Ek-Rylander, Goran Andersson, (2005) Proteolytic Excision of a Repressive Loop Domain in Tartrate-resistant Acid Phosphatase by Cathepsin Kin Osteoclasts. The Journal of Biological Chemistry 280, 28370-28381.

DISCLOSURE OF THE INVENTION

Problems to be Solved by the Invention

As described above, although the importance of TRACP5b is increasing, there are many problems in its production. Therefore, the present inventors took advantage of the characteristics of silkworms, and examined the expression of human TRACP5b by silkworms. Thus, an objective of the present invention is to provide methods for producing a large amount of TRACP5b by using silkworms.

Means for Solving the Problems

The present inventors conducted a dedicated research to solve the above-mentioned problems. As a result, when the inventors tried to mass produce TRACP5 in silkworms and process this TRACP5 to produce TRACP5b, it was surprisingly discovered that TRACP5b was produced directly from the silk glands of silkworms introduced with the human TRACP5 gene. The present invention was accomplished by this process.

Specifically, the present invention relates to methods for producing TRACP5b in the silk gland of silkworms, and provides [1] to [49] described below:

[1] a method for producing TRACP5b, wherein the method comprises the steps of:
 (a) producing a silkworm into which a DNA encoding TRACP5 is introduced; and
 (b) recovering TRACP5b from the produced silkworm;

[2] a method for producing TRACP5b, wherein the method comprises the steps of:

(a) producing a silkworm which comprises a promoter of a DNA encoding a protein specifically expressed in its silk gland and a DNA encoding TRACP5 whose expression is regulated directly or indirectly by the promoter, and which secretes TRACP5b into the silk gland; and (b) recovering said TRACP5b from the produced silkworm;

[3] the method of [2], wherein the silkworm comprises the DNAs of (i) and (ii):

(i) a DNA encoding a transcriptional regulator, which is operably linked downstream of a promoter of a DNA encoding a protein specifically expressed in the silk gland; and (ii) a DNA encoding TRACP5, which is operably linked downstream of a target promoter of the transcriptional regulator;

[4] the method of [2], wherein the silkworm is produced by crossing the silkworms of (i) and (ii):

(i) a silkworm comprising a DNA encoding a transcriptional regulator, which is operably linked downstream of a promoter of a DNA encoding a protein specifically expressed in the silk gland; and (ii) a silkworm comprising a DNA encoding TRACP5, which is operably linked downstream of a target promoter of the transcriptional regulator;

[5] the method of [3] or [4], wherein the transcriptional regulator is GAL4 and the target promoter is UAS;

[6] the method of any one of [2] to [5], wherein the silk gland is middle silk gland or posterior silk gland;

[7] the method of [6], wherein the promoter of a DNA encoding a protein specifically expressed in the silk gland is a promoter of a DNA encoding a sericin 1 protein or sericin 2 protein;

[7-1] the method of [7], wherein the promoter of a DNA encoding a sericin 1 protein is:

(a) a DNA comprising the nucleotide sequence of SEQ ID NO: 7, or (b) a DNA comprising a nucleotide sequence in which one or more nucleotides have been substituted, deleted, added, and/or inserted in the nucleotide sequence of SEQ ID NO: 7;

[7-2] the method of [7], wherein the promoter of a DNA encoding a sericin 2 protein is:

(a) a DNA comprising the nucleotide sequence of SEQ ID NO: 8, or (b) a DNA comprising a nucleotide sequence in which one or more nucleotides have been substituted, deleted, added, and/or inserted in the nucleotide sequence of SEQ ID NO: 8;

[8] the method of [6], wherein the promoter of a DNA encoding a protein specifically expressed in the silk gland is a promoter of a DNA encoding a fibroin protein;

[8-1] the method of [8], wherein the promoter of a DNA encoding a fibroin protein is:

(a) a DNA comprising the nucleotide sequence of SEQ ID NO: 9, or (b) a DNA comprising a nucleotide sequence in which one or more nucleotides have been substituted, deleted, added, and/or inserted in the nucleotide sequence of SEQ ID NO: 9;

[9] the method of any one of [1] to [8-1], wherein TRACP5 comprises a signal sequence;

[10] a method for producing a silkworm that secretes TRACP5b, which comprises the step of introducing a DNA encoding TRACP5 into a silkworm;

[11] a method for producing a silkworm that secretes TRACP5b, which comprises the step of introducing a DNA encoding TRACP5 into a silkworm egg;

[12] a method for producing a silkworm that secretes TRACP5b into the silk gland, which comprises the step of producing a silkworm egg which comprises a promoter of a DNA encoding a protein specifically expressed in the silk gland, and a DNA encoding TRACP5 whose expression is regulated directly or indirectly by the promoter;

[13] the method of [12], wherein the silkworm comprises the DNAs of (i) and (ii):

(i) a DNA encoding a transcriptional regulator, which is operably linked downstream of a promoter of a DNA encoding a protein specifically expressed in the silk gland; and (ii) a DNA encoding TRACP5, which is operably linked downstream of a target promoter of the transcriptional regulator;

[14] the method of [12], wherein the silkworm is produced by crossing the silkworms of (i) and (ii):

(i) a silkworm comprising a DNA encoding a transcriptional regulator, which is operably linked downstream of a promoter of a DNA encoding a protein that is specifically expressed in the silk gland; and (ii) a silkworm comprising a DNA encoding TRACP5, which is operably linked downstream of a target promoter of the transcriptional regulator;

[15] the method of [13] or [14], wherein the transcriptional regulator is GAL4 and the target promoter is UAS;

[16] the method of any one of [12] to [15], wherein the silk gland is middle silk gland or posterior silk gland;

[17] the method of [16], wherein the promoter of a DNA encoding a protein that is specifically expressed in the silk gland is a promoter of a DNA encoding a sericin 1 protein or sericin 2 protein;

[17-1] the method of [17], wherein the promoter of a DNA encoding a sericin 1 protein is:

(a) a DNA comprising the nucleotide sequence of SEQ ID NO: 7, or (b) a DNA comprising a nucleotide sequence in which one or more nucleotides have been substituted, deleted, added, and/or inserted in the nucleotide sequence of SEQ ID NO: 7;

[17-2] the method of [17], wherein the promoter of a DNA encoding a sericin 2 protein is:

(a) a DNA comprising the nucleotide sequence of SEQ ID NO: 8, or (b) a DNA comprising a nucleotide sequence in which one or more nucleotides have been substituted, deleted, added, and/or inserted in the nucleotide sequence of SEQ ID NO: 8;

[18] the method of [16], wherein the promoter of a DNA encoding a protein that is specifically expressed in the silk gland is a promoter of a DNA encoding a fibroin protein;

[18-1] the method of [18], wherein the promoter of a DNA encoding a fibroin protein is:

(a) a DNA comprising the nucleotide sequence of SEQ ID NO: 9, or (b) a DNA comprising a nucleotide sequence in which one or more nucleotides have been substituted, deleted, added, and/or inserted in the nucleotide sequence of SEQ ID NO: 9;

[19] the method of any one of [10] to [18-1], wherein TRACP5 comprises a signal sequence;

[20] a silkworm which comprises a DNA encoding TRACP5, and secretes TRACP5b;

[21] a silkworm which comprises a promoter of a DNA encoding a protein that is specifically expressed in the silk gland and a DNA encoding TRACP5 whose expression is regulated directly or indirectly by the promoter, and which secretes TRACP5b into the silk gland;

[22] the silkworm of [21], which comprises the DNAs of (i) and (ii):

(i) a DNA encoding a transcriptional regulator, which is operably linked downstream of a promoter of a DNA encoding a protein specifically expressed in the silk gland; and (ii) a DNA encoding TRACP5, which is operably linked downstream of a target promoter of the transcriptional regulator;

[23] the silkworm of [21], which is produced by crossing the silkworms of (i) and (ii):

(i) a silkworm comprising a DNA encoding a transcriptional regulator, which is operably linked downstream of a promoter of a DNA encoding a protein that is specifically expressed in the silk gland; and (ii) a silkworm comprising a DNA encoding TRACP5, which is operably linked downstream of a target promoter of the transcriptional regulator;

[24] the silkworm of [22] or [23], wherein the transcriptional regulator is GAL4 and the target promoter is UAS;

[25] the silkworm of any one of [21] to [24], wherein the silk gland is a middle silk gland or a posterior silk gland;

[26] the silkworm of [25], wherein the promoter of a DNA encoding a protein that is specifically expressed in the silk gland is a promoter of a DNA encoding a sericin 1 protein or sericin 2 protein;

[26-1] the silkworm of [26], wherein the promoter of a DNA encoding a sericin 1 protein is:

(a) a DNA comprising the nucleotide sequence of SEQ ID NO: 7, or (b) a DNA comprising a nucleotide sequence in which one or more nucleotides have been substituted, deleted, added, and/or inserted in the nucleotide sequence of SEQ ID NO: 7;

[26-2] the silkworm of [26], wherein the promoter of a DNA encoding a sericin 2 protein is:

(a) a DNA comprising the nucleotide sequence of SEQ ID NO: 8, or (b) a DNA comprising a nucleotide sequence in which one or more nucleotides have been substituted, deleted, added, and/or inserted in the nucleotide sequence of SEQ ID NO: 8;

[27] the silkworm of [25], wherein the promoter of a DNA encoding a protein that is specifically expressed in the silk gland is a promoter of a DNA encoding a fibroin protein;

[27-1] the silkworm of [27], wherein the promoter of a DNA encoding a fibroin protein is:

(a) a DNA comprising the nucleotide sequence of SEQ ID NO: 9, or (b) a DNA comprising a nucleotide sequence in which one or more nucleotides have been substituted, deleted, added, and/or inserted in the nucleotide sequence of SEQ ID NO: 9;

[28] the silkworm of any one of [20] to [27-1], wherein TRACP5 comprises a signal sequence;

[29] a silkworm that comprises a DNA encoding TRACP5 which is operably linked downstream of a target promoter of a transcriptional regulator;

[30] the silkworm of [29], wherein the transcriptional regulator is GAL4 and the target promoter is UAS;

[31] the silkworm of [29] or [30], wherein TRACP5 comprises a signal sequence;

[32] the method of any one of [1] to [9], wherein TRACP5b is used in a screening for a candidate compound for a TRACP5b-specific inhibitor, activator, or modulator;

[33] the method of [32], wherein the TRACP5b-specific inhibitor, activator, or modulator is used for treating a disease related to increased bone resorption;

[34] the method of [33], wherein the disease related to increased bone resorption is selected from the group consisting of a tissue disorder, metabolic bone disease, and osteoporosis;

[35] a method for producing TRACP5b, comprising the steps of:

(a) producing a silkworm which comprises a promoter of a DNA encoding a cytoplasmic actin protein and a DNA encoding TRACP5 whose expression is regulated directly or indirectly by the promoter, and which secretes TRACP5b into the fat body; and (b) recovering said TRACP5b from the produced silkworm;

[36] the method of [35], wherein the silkworm comprises the DNAs of (i) and (ii):

(i) a DNA encoding a transcriptional regulator, which is operably linked downstream of a promoter of a DNA encoding a cytoplasmic actin protein; and (ii) a DNA encoding TRACP5, which is operably linked downstream of a target promoter of the transcriptional regulator;

[37] the method of [35], wherein the silkworm is produced by crossing the silkworms of (i) and (ii):

(i) a silkworm comprising a DNA encoding a transcriptional regulator, which is operably linked downstream of a promoter of a DNA encoding a cytoplasmic actin protein; and (ii) a silkworm comprising a DNA encoding TRACP5b, which is operably linked downstream of a target promoter of the transcriptional regulator;

[38] the method of [36] or [37], wherein the transcriptional regulator is GAL4 and the target promoter is UAS;

[38-1] the method of [38], wherein the promoter of a DNA encoding a cytoplasmic actin protein is:

(a) a DNA comprising the nucleotide sequence of SEQ ID NO: 10, or (b) a DNA comprising a nucleotide sequence in which one or more nucleotides have been substituted, deleted, added, and/or inserted in the nucleotide sequence of SEQ ID NO: 10;

[39] the method of any one of [35] to [38-1], wherein TRACP5 comprises a signal sequence;

[40] a method for producing a silkworm that secretes TRACP5b into the fat body, comprising the step of producing a silkworm egg that comprises a promoter of a DNA encoding a cytoplasmic actin protein and a DNA encoding TRACP5 whose expression is regulated directly or indirectly by the promoter;

[41] the method of [40], wherein the silkworm comprises the DNAs of (i) and (ii):

(i) a DNA encoding a transcriptional regulator, which is operably linked downstream of a promoter of a DNA encoding a cytoplasmic actin protein; and (ii) a DNA encoding TRACP5, which is operably linked downstream of a target promoter of the transcriptional regulator;

[42] the method of [40], wherein the silkworm is produced by crossing the silkworms of (1) and (ii):

(i) a silkworm comprising a DNA encoding a transcriptional regulator, which is operably linked downstream of a promoter of a DNA encoding a cytoplasmic actin protein; and (ii) a silkworm comprising a DNA encoding TRACP5, which is operably linked downstream of a target promoter of the transcriptional regulator;

[43] the method of [41] or [42], wherein the transcriptional regulator is GAL4 and the target promoter is UAS;

[43-1] the method of [43], wherein the promoter of a DNA encoding a cytoplasmic actin protein is:

(a) a DNA comprising the nucleotide sequence of SEQ ID NO: 10, or (b) a DNA comprising a nucleotide sequence in which one or more nucleotides have been substituted, deleted, added, and/or inserted in the nucleotide sequence of SEQ ID NO: 10;

[44] the method of any one of [40] to [43-1], wherein TRACP5 comprises a signal sequence;
[45] a silkworm which comprises a promoter of a DNA encoding a cytoplasmic actin protein and a DNA encoding TRACP5 whose expression is regulated directly or indirectly by the promoter, and which secretes TRACP5b into the fat body;
[46] the silkworm of [45], which comprises the DNAs of (i) and (ii):
 (i) a DNA encoding a transcriptional regulator, which is operably linked downstream of a promoter of a DNA encoding a cytoplasmic actin protein; and
 (ii) a DNA encoding TRACP5, which is operably linked downstream of a target promoter of the transcriptional regulator;
[47] the silkworm of [45], which is produced by crossing the silkworms of (i) and (ii):
 (i) a silkworm comprising a DNA encoding a transcriptional regulator, which is operably linked downstream of a promoter of a DNA encoding a cytoplasmic actin protein; and
 (ii) a silkworm comprising a DNA encoding TRACP5, which is operably linked downstream of a target promoter of the transcriptional regulator;
[48] the silkworm of [46] or [47], wherein the transcriptional regulator is GAL4 and the target promoter is UAS;
[48-1] the silkworm of [48], wherein the promoter of a DNA encoding a cytoplasmic actin protein is:
 (a) a DNA comprising the nucleotide sequence of SEQ ID NO: 10, or
 (b) a DNA comprising a nucleotide sequence in which one or more nucleotides have been substituted, deleted, added, and/or inserted in the nucleotide sequence of SEQ ID NO: 10; and
[49] the silkworm of any one of [45] to [48-1], wherein TRACP5 comprises a signal sequence.

MODE FOR CARRYING OUT THE INVENTION

Figure 1:
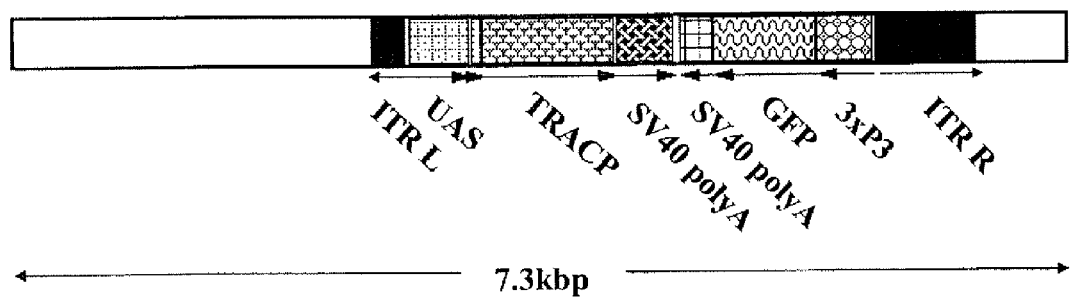
FIG. 1 shows the structure of the pBMCSUASsigTRACP vector for producing transgenic silkworms.

The present invention relates to methods for producing TRACP5b using silkworms. The present invention is based on the present inventors' success in producing active TRACP5b within silkworms. More specifically, the present invention provides methods for producing TRACP5b comprising the steps of:
 (a) producing a silkworm into which a DNA encoding TRACP5 has been introduced; and
 (b) recovering TRACP5b from the produced silkworm.
Examples of TRACP5 used in the present invention include human-, mouse-, and rat-derived TRACP5. In the present invention, a DNA encoding TRACP5 is not limited in any way so long as the silkworm carrying it secretes TRACP5b into the silk gland; however, human-derived TRACP5 is preferred from application aspects. Specifically, an example is a DNA comprising a nucleotide sequence encoding the amino acid sequence of SEQ ID NO: 5. Another example is a DNA comprising a nucleotide sequence encoding a protein which has a tartrate-resistant acid phosphatase activity and has an amino acid sequence with one or more amino acid substitutions, deletions, additions, and/or insertions in the amino acid sequence of SEQ ID NO: 5. Whether or not the protein obtained from the DNA has TRACP5b activity can be determined by binding the sample to a monoclonal antibody against TRACP5b and then assaying the bound TRACP5b using a substrate for TRACP5b at its optimum pH, as described in PCT international publications WO04/59320 and WO04/77059, and Japanese Patent Application Kohyo Publication No. (JP-A) 2002-510050 (unexamined Japanese national phase publication corresponding to non-Japanese international publication).

Methods for preparing a protein functionally equivalent to a certain protein that are well known to those skilled in the art include methods for introducing mutations into a polypeptide. For example, one skilled in the art can prepare a protein functionally equivalent to TRACP5b by introducing appropriate mutations into TRACP5 using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766). Amino acid mutations may also occur naturally. Therefore, DNAs comprising a nucleotide sequence encoding a protein that has an amino acid sequence with one or more amino acid mutations in the amino acid sequence of TRACP5 and is functionally equivalent to TRACP5 is also used to produce TRACP5b of the present invention. The number of mutated amino acids in such mutants may be generally 50 amino acids or less, preferably 30 amino acids or less, and more preferably 10 amino acids or less (for example, 5 amino acids or less).

Amino acid residues are preferably mutated to other amino acids in which the properties of the amino acid side chains are conserved. The properties of amino acid side chains include: hydrophobic amino acids (A, I, L, M, F, P, W, Y, and V), hydrophilic amino acids (R, D, N, C, E, Q, Q, H, K, S, and T), amino acids with aliphatic side chains (G, A, V, L, I, and P); amino acids with hydroxyl-containing side chains (S, T, and Y); amino acids with sulfur atom-containing side chains (C and M); amino acids with carboxylic acid- and amide-containing side chains (D, N, E, and Q); amino acids with basic side chains (R, K, and H); and amino acids with aromatic group-containing side chains (H, F, Y, and W) (amino acids are represented by one-letter codes in parentheses).

A polypeptide comprising a modified amino acid sequence, in which one or more amino acid residues are deleted, added, and/or replaced with other amino acids in a certain amino acid sequence, is known to retain its original biological activity (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

In the present invention, the DNA encoding TRACP5 may have a secretion signal (signal sequence) for maintaining the activity of the produced TRACP5b or for promoting its secretion to increase the amount of recovery. Secretory proteins or integral membrane proteins must pass through a lipid bilayer after they are synthesized in endoplasmic reticulum membrane-bound ribosomes. Signal sequences refer to amino acid residues located at the N terminal of protein that are necessary at this time.

Signal sequences in the present invention are not particularly limited so long as they have the above-mentioned function. For example, signal sequences derived from humans, mice, rats, rabbits, donkeys, goats, horses, birds, dogs, cats, yeasts, and insects may be preferably used.

Preferred signal sequences of the present invention also include, for example, TRACP5 signal sequences. The origin of TRACP5 is not particularly limited and includes, for example, TRACP5 derived from humans, mice, rats, rabbits, donkeys, goats, horses, birds, dogs, and cats. When human TRACP5b is produced in the present invention, a human TRACP5 signal sequence is particularly preferred. The use of these signal sequences enables efficient production of the expressed TRACP5b.

The human-derived TRACP5 signal sequence includes a protein comprising the amino acid sequence of SEQ ID NO: 6. Furthermore, an amino acid sequence with one or more amino acid substitutions, deletions, additions, and/or insertions in the amino acid sequence of SEQ ID NO: 6 may also be used as the signal sequence so long as the sequence has an activity equivalent to the protein of SEQ ID NO: 6. Herein, the phrase "functionally equivalent" means that a protein of interest has a biological or biochemical activity similar to that of a protein comprising the amino acid sequence of SEQ ID NO: 6.

In the present invention, a signal sequence is, without limitation, preferably linked to the N terminus of TRACP5b.

TRACP5b produced by the methods of the present invention is not limited in any way so long as it is produced by the methods of the present invention, and it may or may not comprise a signal sequence. More specifically, TRACP5b produced by the production methods of the present invention includes both TRACP5b with and without a signal sequence.

TRACP5b produced in the present invention is not particularly limited so long as it is transcribed from a DNA encoding TRACP5 and is an enzyme having an osteoclast-derived TRACP5 activity, namely, TRACP5b activity. The presence or absence of TRACP5b activity can be determined by TRACP5b assay methods well known to those skilled in the art. TRACP5b produced in the present invention is preferably used in the screening for candidate compounds for TRACP5b-specific inhibitors, activators, or modulators. Furthermore, when activity staining is carried out in acidic disc electrophoresis, TRACP5b preferably shows a band in the bottom cathode side, at a position same as that of the tartrate-resistant acid phosphatase obtained from osteoclasts. An example of the DNA encoding TRACP5 is a DNA comprising the nucleotide sequence of SEQ ID NO: 4.

Herein below, methods for producing TRACP5b of the present invention will be more specifically described. In the methods for producing TRACP5b of the present invention, first, silkworms introduced with a DNA encoding TRACP5 are produced. Methods for producing silkworms introduced with a DNA encoding TRACP5 include, but are not limited to, for example:
(i) a method for producing a transgenic silkworm which comprises a promoter of a DNA encoding a protein that is specifically expressed in the silk gland and a DNA encoding TRACP5 whose expression is regulated directly or indirectly by the promoter, and which secretes TRACP5b into the silk gland (first example); and
(ii) a method for production by preparing a virus comprising a DNA encoding TRACP5 and then infecting silkworms with the virus (second example).

In the present invention, when the method for production by preparing a virus comprising a DNA encoding TRACP5 and then infecting silkworms with the virus (second example) is used as the method for producing silkworms introduced with a DNA encoding TRACP5, it can be performed, for example, by the method of JP-A (Kokai) H07-289270. More specifically, the production can be carried out by preparing a virus (preferably baculovirus, and more preferably silkworm nucleopolyhedrovirus) containing a nucleotide sequence in which all or a part of the structural protein gene in the viral DNA is linked with TRACP5, and then infecting silkworms with the virus.

When the second example is used, methods for recovering TRACP5b from the produced silkworm include methods of recovering TRACP5b by extracting the body fluid of the silkworm. Specifically, for example, TRACP5b can be recovered by cutting the abdomen of the silkworm, extracting the body fluid with cold water, and purifying it.

In the TRACP5b production method of the present invention, the first example mentioned above is preferred in that a large amount of TRACP5b can be simply produced. Hereinafter, the first example will be described in detail.

A specific preferred embodiment of the method for producing TRACP5b of the present invention is characterized in that TRACP5b is produced in the silk gland of silkworms. More specifically, the present invention relates to methods for producing TRACP5b comprising the steps (a) and (b) below:
(a) producing a silkworm which comprises a promoter of a DNA encoding a protein specifically expressed in the silk gland and a DNA encoding TRACP5 whose expression is regulated directly or indirectly by the promoter, and which secretes TRACP5b into the silk gland; and
(b) collecting the TRACP5b from the produced silkworm.

In the step of producing the silkworms of the present invention, for example, a promoter of a DNA encoding a protein specifically expressed in the silk gland and a DNA encoding TRACP5 whose expression is regulated directly or indirectly by the promoter are introduced into silkworm eggs.

Next, silkworms that secrete TRACP5b into the silk gland are selected from silkworms that have hatched from the produced silkworm eggs.

In the present invention, silkworms are selected, for example, by using selection markers. Markers that are commonly used by those skilled in the art, including fluorescent proteins such as CFP, GFP, YFP, and DsRed, can be used as selection markers in the present invention. Using these markers, silkworms can be detected by simply observing them with a fluorescence stereomicroscope. Furthermore, multiple markers can be used simultaneously since each fluorescent color is different.

An example of the DNA encoding TRACP5 is a DNA comprising the nucleotide sequence of SEQ ID NO: 4. TRACP5b can be secreted into the silk gland of a silkworm by introducing into the silkworm a vector into which such a DNA has been inserted.

In the present invention, TRACP5b is secreted into the silk gland. The silk gland is an organ that exists in pairs in the silkworm body, and synthesizes silk proteins. The silk gland can be divided into the posterior, middle, and anterior silk glands, and silk protein synthesis takes place in the posterior and middle silk glands. In the present invention, the middle and posterior silk glands are preferred.

In the present invention, the silkworm egg comprising a promoter of a DNA encoding a protein that is specifically expressed in the silk gland and a DNA encoding TRACP5 whose expression is regulated directly by the promoter includes, for example, a silkworm egg comprising a DNA in which a TRACP5-encoding DNA is operably linked downstream of a promoter of a DNA encoding a protein that is specifically expressed in the silk gland. Such a silkworm egg can be produced by introducing into a silkworm egg a DNA in which a TRACP5-encoding DNA is operably linked downstream of a promoter of a DNA encoding a protein that is specifically expressed in the silk gland.

In the present invention, the silkworm egg comprising a promoter of a DNA encoding a protein that is specifically expressed in the silk gland and a DNA encoding TRACP5 whose expression is regulated indirectly by the promoter includes, for example, a silkworm egg comprising:
(i) a DNA in which a DNA encoding a transcriptional regulator is operably linked downstream of a promoter of a DNA encoding a protein that is specifically expressed in the silk gland; and
(ii) a DNA in which a TRACP5-encoding DNA is operably linked downstream of a target promoter of the transcriptional regulator.

In the present invention, the DNA encoding TRACP5 whose expression is regulated directly or indirectly by a promoter of a DNA encoding a protein that is specifically expressed in the silk gland may comprise a signal sequence to promote TRACP5b secretion and increase the amount of recovery. Specific embodiments of the signal sequence are described above.

The phrase "operably linked" means that a promoter and a DNA are linked such that expression of the DNA located downstream of the promoter is induced by the binding of a transcriptional regulator to the promoter. Therefore, even if the DNA is linked to another gene and a fusion protein is produced from the linked genes, as long as the expression of the fusion protein is induced by the binding of the transcriptional regulator to the promoter, this DNA can be considered to be "operably linked" as described above.

Examples of the combination of the transcriptional regulator and target sequence include GAL4 and UAS, and TetR and TRE. By using GAL4 and UAS, or TetR and TRE, the expression site, timing, and level of a gene of interest can be regulated precisely, and the gene can be easily expressed in many tissues. Furthermore, a strain can be established even if a gene to be expressed is a lethal gene.

A variety of methods can be selected as methods for producing the above-mentioned silkworm eggs. For example, the above-described DNAs of (i) and (ii) can be introduced into separate silkworm eggs. Silkworm eggs comprising both DNAs can be obtained by crossing the silkworms with each other that are derived from the silkworm eggs into which the individual DNAs have been introduced. In this case, the tissue of expression, expression timing and level and such can be adjusted by the transcriptional regulators. Therefore, this method is advantageous in that by crossing with a strain into which a gene to be expressed has been introduced, the tissue of expression, expression timing and level and such can be altered without generating many strains. Experiments can still be carried out despite the infertility that may be caused by expression of the gene of interest. An additional advantage is an increased level of the product of the introduced gene compared to when a single promoter is used. Alternatively, silkworm eggs comprising the DNAs of (i) and (ii) can be obtained by artificially introducing one of the DNAs into eggs oviposited by a silkworm into which the other DNA has been introduced. Silkworm eggs comprising the DNAs of (i) and (ii) can also be obtained by introducing both DNAs into the same egg (Imamura, M., Nakai, J., Inoue, S., Quan, G.-X., Kanda, T. and Tamura, T. (2003) Targeted gene expression using the GAL4/UAS system in the silkworm *Bombyx mori*. Fourth International Workshop on Transgenesis and Genomics of Invertegrate Organisms, Asilomar, p. 53).

DNAs can be introduced into silkworm eggs, for example, according to the method for injecting transposons as vectors into silkworm eggs in the early developmental stage (Tamura, T., Thibert, C., Royer, C., Kanda, T., Abraham, E., Kamba, M., Komoto, N., Thomas, J.-L., Mauchamp, B., Chavancy, G, Shirk, P., Fraser, M., Prudhomme, J.-C. and Couble, P., 2000, Nature Biotechnology 18, 81-84). For example, vectors in which the above-described DNAs have been inserted into inverted terminal repeats of the transposons (Handler A M, McCombs S D, Fraser M J, Saul S H. (1998) Proc. Natl. Acad. Sci. U.S.A. 95(13): 7520-5) are introduced into silkworm eggs along with vectors comprising DNAs encoding transposases (helper vectors). An example of a helper vector is pHA3PIG (Tamura, T., Thibert, C., Royer, C., Kanda, T., Abraham, E., Kamba, M., Komoto, N., Thomas, J.-L., Mauchamp, B., Chavancy, G, Shirk, P., Fraser, M., Prudhomme, J.-C. and Couble, P., 2000, Nature Biotechnology 18, 81-84), but is not limited thereto.

An example of the transposons of the present invention is preferably piggyBac, but is not limited thereto. Transposons such as mariner and minos may be used (Shimizu, K., Kamba, M., Sonobe, H., Kanda, T., Klinakis, A. G., Savakis, C. and Tamura, T. (2000) Insect Mol. Biol., 9, 277-281; Wang W, Swevers L, Iatrou K. (2000) Insect Mol Biol 9 (2): 145-55).

In the middle silk gland, a promoter of a DNA encoding a protein that is specifically expressed in the silk gland in the present invention is, for example, a promoter of a DNA encoding the sericin 1 protein or sericin 2 protein. Examples of a promoter of a DNA encoding the sericin I protein or sericin 2 protein include DNAs comprising the nucleotide sequence of SEQ ID NO: 7 or 8. Examples of the DNAs comprising the nucleotide sequence of SEQ ID NO: 7 or 8 are DNAs consisting of the nucleotide sequence of SEQ ID NO: 7 or 8, and DNAs comprising the upstream regions or downstream regions of DNAs consisting of the nucleotide sequence of SEQ ID NO: 7 or 8, but are not limited thereto. The upstream regions and downstream regions of DNAs consisting of the nucleotide sequence of SEQ ID NO: 16 or 17 are disclosed in references: Okamoto, H., Ishikawa, E. and Suzuki, Y. (1982) Structural analysis of sericin genes. Homologies with fibroin gene in the 5' flanking nucleotide sequences. J. Biol. Chem., 257, 15192-15199; Garel, A., Deleage, G. and Prudhomme, J. C. (1997) Structure and organization of the *Bombyx mori* sericin 1 gene and of the sericins 1 deduced from the sequence of the Ser 1B cDNA. Insect Biochem. Mol. Biol., 27, 469-477; Michaille, J. J., Garel, A. and Prudhomme, J. C. (1990) Cloning and characterization of the highly polymorphic Ser2 gene of *Bombyx mori*. Gene, 86, 177-184.

Furthermore, in the present invention, an example of a promoter of a DNA encoding a protein that is specifically expressed in the middle silk gland, may be a DNA that is structurally similar to a DNA comprising the nucleotide sequence of SEQ ID NO: 7 or 8, and that has an equivalent or improved promoter activity compared to the activity of a DNA comprising the nucleotide sequence of SEQ ID NO: 7 or 8. Such a DNA may be, for example, a DNA comprising a nucleotide sequence with one or more nucleotide substitutions, deletions, additions, and/or insertions in the nucleotide sequence of SEQ ID NO: 7 or 8. This DNA can be produced by methods such as hybridization techniques, polymerase chain reaction (PCR) techniques, site-directed mutagenesis, and DNA synthesis. Whether the prepared DNAs have promoter activity can be examined by those skilled in the art, for example, using well-known reporter assays with reporter genes.

The reporter genes are not particularly limited as long as their expression is detectable, and include the CAT gene, lacZ gene, luciferase gene, β-glucuronidase gene (GUS), and GFP gene, which are generally used by those skilled in the art. The expression level of the reporter genes can be measured according to the type of the reporter genes by methods well known to those skilled in the art. For example, when the reporter gene is the CAT gene, the expression level of the reporter gene can be measured by detecting the acetylation of chloramphenicol catalyzed by the gene product. When the reporter gene is the lacZ gene, luciferase gene, β-glucuronidase gene (GUS), or GFP gene, the expression level of the reporter gene can be measured by, respectively, detecting the color development of pigment compound as a result of the catalytic action of the gene expression product; detecting the fluorescence of fluorescent compound as a result of the catalytic action of the gene expression product; detecting the luminescence of Glucuron (ICN) or the color development of 5-bromo-4-chloro-3-indolyl-β-glucuronide (X-Gluc) as a result of the catalytic action of the gene expression product; or detecting the fluorescence of the GFP protein.

On the other hand, in the present invention, a promoter of a DNA encoding a protein that is specifically expressed in the posterior silk gland is, for example, a promoter of a DNA encoding the fibroin L chain protein. Examples of a promoter of a DNA encoding the fibroin L chain protein include DNAs comprising the nucleotide sequence of SEQ ID NO: 9. Examples of a DNA comprising the nucleotide sequence of SEQ ID NO: 9 include DNAs consisting of the nucleotide sequence of SEQ ID NO: 9, and DNAs comprising upstream regions or downstream regions of DNAs consisting of the nucleotide sequence of SEQ ID NO: 9, but are not limited thereto. The upstream regions and downstream regions of DNAs consisting of the nucleotide sequence of SEQ ID NO: 9 are disclosed in KIKUCHI, Y., K. MORI, S. SUZUKI, K. YAMAGUCHI and S. MIZUNO, 1992 Structure of the *Bombyx mori* fibroin light-chain-encoding gene: upstream sequence elements common to the light and heavy chain. Gene 110: 151-158).

Furthermore, in the present invention, a promoter of a DNA encoding a protein that is specifically expressed in the posterior silk gland is, for example, a DNA which is structurally similar to a DNA comprising the nucleotide sequence of SEQ ID NO: 9 and has an equivalent or improved promoter activity compared to a DNA comprising the nucleotide sequence of SEQ ID NO: 9. Such promoters can be prepared by methods described above.

Methods of the present invention for producing TRACP5b comprise the step of recovering TRACP5b synthesized in the silkworm body. Synthesized TRACP5b is secreted into the middle or posterior silk gland in its active form without being insolubilized. Therefore, TRACP5b can be recovered from the middle or posterior silk gland. In the method for recovering TRACP5b from the middle or posterior silk gland, for example, silkworms are dissected at the spinning stage, the middle or posterior silk gland is removed and placed in 20 mM Tris-HCl pH7.4, and then the silk gland is cut with a pair of tweezers or a scalpel to recover TRACP5b from the silk gland; however, the method is not limited thereto.

The purification of TRACP5b from a protein solution extracted from the silk gland is, for example, carried out as follows. The extract is applied to a CM-Sepharose column and eluted with a linear gradient of different salt concentrations. These eluted fractions are assayed for TRACP5b activity, and fractions having TRACP5b activity are recovered and concentrated using a spin column. Then the obtained solution with TRACP5b activity is subjected to gel filtration using a Superdex200 column, and fractions having TRACP5b activity are collected and concentrated in the same manner. Furthermore, purification is performed on a heparin column (Hi-Trap Heparin HP, GE Healthcare) using a linear gradient of various salt concentrations, and fractions having TRACP5b activity are concentrated using a spin column in the same manner. The presence or absence of TRACP5b and the purification status in these fractions can be confirmed, for example, by acidic electrophoresis.

The TRACP5b of the present invention can also be recovered, for example, from cocoons spun by the silkworms. Examples of methods for recovering proteins include, but are not limited to, methods well known to those skilled in the art, such as the method in which cocoons are dissolved in 60% LiSCN and then dialyzed in 20 mM Tris and 5 M urea to recover proteins (Inoue, S., Tsuda, H., Tanaka, H., Magoshi, Y., and Mizuno (2001) Sericologia 4, 157-163). Other feasible recovery methods include methods using surfactants and methods comprising the step of dissolving in aqueous solutions.

The silkworms of the present invention are not particularly limited. However, in order to produce large amounts of TRACP5b, it is preferable to use silkworms in which the production of proteins constituting the silk thread, such as the fibroin protein, is suppressed by mutations in DNA regions (including coding regions, promoter regions, and untranslated regions) that encode the proteins constituting the silk thread. Examples of such silkworms include mutant silkworm strains in which the production of proteins constituting the silk thread is suppressed by mutations in DNA regions encoding these proteins; and preferably include exarate pupae of silkworms in which the production of proteins constituting the silk thread is suppressed by such mutations; or more preferably include the silkworm strain Nd-s$^D$, but are not limited thereto. In the present invention, any silkworms are appropriate as long as the production of proteins constituting the silk thread is suppressed, regardless of whether suppression of the production of such proteins is caused artificially or depends on naturally-occurring mutations.

An embodiment of such silkworms is a silkworm well known to those skilled in the art as "sericin silkworm". The use of sericin silkworms enables mass production of TRACP5b in the middle silk gland, and also facilitates purification of TRACP5b synthesized from DNAs encoding TRACP5 which have been introduced into the chromosome. Furthermore, when producing TRACP5b in the posterior silk gland, sericin silkworms are preferably used in terms of the amount of production.

Silkworms having the characteristic of ovipositing nondiapausing eggs, as well as silkworms having the characteristic of ovipositing diapausing eggs (for example, silkworm varieties for practical use, including Gunma, 200, Shunrei, Shogetsu, Kinshu, and Showa) can be used as the silkworms of the present invention. Herein, the term "diapausing eggs" refers to eggs in which embryogenesis after oviposition is transiently stopped, and the term "nondiapausing eggs" refers to eggs in which embryogenesis after oviposition does not stop, and leads to larval hatching.

When silkworms having the characteristic of ovipositing diapausing eggs are used, DNAs are introduced into the nondiapausing eggs after they have been laid. For example, the silkworm variety Gunma can be induced to oviposit nondiapausing eggs, by methods of culturing diapausing eggs at 15°

C. to 21° C. to induce adults hatched from the diapausing eggs to oviposit nondiapausing eggs, preferably by methods of culturing diapausing eggs at 16° C. to 20° C. to induce adults hatched from the diapausing eggs to oviposit nondiapausing eggs, more preferably by methods of culturing diapausing eggs at 18° C. to induce adults hatched from the diapausing eggs to oviposit nondiapausing eggs, and most preferably by methods of culturing diapausing eggs at 18° C. and rearing larvae hatched from the diapausing eggs under continuous light to induce the reared adults to oviposit nondiapausing eggs. The silkworm variety 200 can be induced to oviposit nondiapausing eggs by, without limitation, methods of culturing diapausing eggs at 15° C. to 21° C. to induce adults hatched from the diapausing eggs to oviposit nondiapausing eggs, preferably by methods of culturing diapausing eggs at 16° C. to 20° C. to induce adults hatched from the diapausing eggs to oviposit nondiapausing eggs, more preferably by methods of culturing diapausing eggs at 18° C. to induce adults hatched from the diapausing eggs to oviposit nondiapausing eggs, or by methods of rearing larvae hatched from diapausing eggs under continuous light to induce the reared adults to oviposit nondiapausing eggs, and most preferably by methods of culturing diapausing eggs at 25° C. and rearing larvae hatched from the diapausing eggs under continuous light to induce the reared adults to oviposit nondiapausing eggs.

The eggs can be cultured in an incubator at 18° C. to 25° C. or in a constant temperature room. Larvae can be reared on an artificial diet in a breeding room at 20° C. to 29° C.

The diapausing eggs of the present invention as described above can be cultured according to methods for culturing silkworm eggs common to those skilled in the art. For example, culturing can be performed using the method described in "Monbusho (Ministry of Education) (1978) Sanshu Seizo (Production of silkworm varieties) p. 193, Jikkyo Shuppan, Tokyo." The silkworm larvae of the present invention can be reared by methods well known to those skilled in the art. For example, silkworm larvae are reared according to the method described in "Monbusho (Ministry of Education) (1978) Sanshu Seizo (Production of silkworm varieties) p. 193, Jikkyo Shuppan, Tokyo."

In the present invention, whether oviposited eggs are nondiapausing eggs can be determined from the color of the eggs. It is generally known that diapausing eggs are dark brown in color and nondiapausing eggs are pale yellow. Therefore, in the present invention, oviposited eggs are determined to be nondiapausing eggs if the color is not dark brown, and preferably if the color is pale yellow.

Herein below, examples of methods for introducing DNAs into silkworm eggs will be specifically described, but methods of the present invention for introducing DNAs into silkworm eggs are not limited thereto. For example, DNAs can be introduced directly into silkworm eggs using a DNA injection tube. In a preferred embodiment, a hole is made physically or chemically in an eggshell in advance, and then DNAs are introduced through this hole. In this case, a DNA injection tube can be inserted into the egg through the hole by adjusting the insertion angle to be nearly perpendicular to the ventral surface of the egg.

In the present invention, examples of the methods for physically making a hole in an eggshell include hole making methods that use needles, microlasers or such. Preferably, a hole can be made in an eggshell by methods using needles. The material, strength and such of the needles are not particularly limited, as long as the needles can make a hole in a silkworm eggshell. The needles in the present invention ordinarily refer to rod-shaped needles having a sharp tip, but are not limited to this form. As long as the needles can make a hole in an eggshell, there are no particular limitations on their overall shape. For example, a pyramid-shaped object with a sharp tip, and a cone-shaped object with a sharp tip are also included in the "needles" of this invention. In the present invention, tungsten needles can be preferably used. The needles of the present invention have enough thickness (diameter) to make holes that allow a capillary, as described below, to pass through. The needle thickness is generally 2 to 20 μm, and preferably 5 to 10 μm. On the other hand, examples of methods for chemically making a hole in an eggshell include hole making methods that use chemical agents (for example, hypochlorous acid) or such.

In the present invention, the position of the hole is not particularly limited as long as a DNA injection tube can be inserted through the hole at an insertion angle that is nearly perpendicular to the ventral surface of the egg. The ventral side and its opposite side of the egg are preferable; the ventral side is more preferable; and the central portion of the ventral side slightly towards the posterior end is more preferable.

In the present invention, the phrase "nearly perpendicular" means 70° to 120°, and preferably 80° to 90°. In the present invention, the phrase "position where germ cells will be developed in the future" usually refers to a position close to the egg surface at the ventral side of the egg (normally 0.01 mm to 0.05 mm beneath the egg surface), and preferably a position near the egg surface at the center of the ventral side of the egg, slightly towards the posterior pole.

In the present invention, the material, strength, internal diameter and such of tubes for injecting DNAs are not particularly limited. However, when a hole is made physically or chemically in an eggshell before insertion of a DNA injection tube, the tube preferably has enough thickness (external diameter) to pass through the opened hole. In the present invention, examples of the DNA injection tube include a glass capillary.

In a preferred embodiment of the DNA introduction methods of the present invention, an all-in-one manipulator equipped with a DNA injection tube and a needle is used to perform the steps of: physically or chemically opening a hole in a silkworm egg; inserting the DNA injection tube through the hole into the egg at an insertion angle nearly perpendicular to the ventral surface of the egg; and injecting DNAs. The present invention is preferably carried out using an apparatus comprising the manipulator as one of the components.

Such an apparatus consists of a dissecting microscope, an illuminator, a movable stage, a coarse manipulator fixed to the microscope with a metal fitting, a micromanipulator attached to this manipulator, and an injector that adjusts the air pressure for DNA injection. The pressure applied by the injector is provided from a nitrogen tank, and a pressure switch can be operated using a foot switch. Injection is performed on eggs immobilized onto a substrate such as a glass slide and the position of the eggs is adjusted using a movable stage. The glass capillary of the micromanipulator is connected to and operated by an operating portion connected to four tubes. Specifically, the position of a tungsten needle relative to an egg is adjusted using the coarse manipulator, and then a hole is made by shifting the egg in the horizontal direction using the stage lever. Next, the lever of the micromanipulator operating portion guides the tip of the glass capillary to the position of the hole, and the capillary is inserted into the egg using the stage lever. In this case, the glass capillary must be inserted perpendicularly to the ventral surface of the egg. The foot switch is then operated to inject DNAs, and the lever is operated to draw out the capillary from the egg. The opened hole is closed using instant adhesive or such, and the egg is protected in an incubator at constant temperature and constant humidity. The apparatus used in the present invention is preferably the apparatus described in U.S. Pat. No. 1,654,050, or a modified version of this apparatus.

Furthermore, in an embodiment of the present invention, silkworm eggs to which DNAs are introduced are preferably immobilized onto a substrate. Examples of the substrate used in the present invention include a glass slide and plastic sheet, but are not particularly limited thereto. In this embodiment of the present invention, the eggs are immobilized preferably after their direction is properly arranged, so that the DNAs can be injected precisely to the position in the silkworm egg where germ cells will be developed in the future. Furthermore, in this embodiment, the number of silkworm eggs immobilized onto the substrate is not particularly limited. When multiple silkworm eggs are used, it is preferable that the silkworm eggs are unidirectionally immobilized onto the substrate in a dorsoventral direction. The immobilization of silkworm eggs to a substrate in the present invention can be performed, for example, by inducing oviposition on commercially available cards (various egg cards) precoated with water-soluble glue, detaching eggs by adding water to the cards, and aligning the wet eggs on a substrate to be air-dried. The eggs are preferably immobilized onto a glass slide so that the eggs are arranged unidirectionally. Immobilization of the eggs onto the substrate can be also accomplished by using a double-sided adhesive tape, adhesive or such.

To confirm whether DNAs have been successfully introduced into silkworm eggs, for example, a method for re-extracting and analyzing the injected DNAs from the eggs (Nagaraju, J., Kanda, T., Yukuhiro, K., Chavancy, G., Tamura, T. and Couble, P. (1996) Attempt of transgenesis of the silkworm (*Bombyx mori* L) by egg-injection of foreign DNA. Appl. Entomol. Zool., 31, 589-598), or a method for observing expression of the injected DNAs in the eggs (Tamura, T., Kanda, T., Takiya, S., Okano, K. and Maekawa, H. (1990) Transient expression of chimeric CAT genes injected into early embryos of the domesticated silkworm, *Bombyx mori*. Jpn. J. Genet., 65, 401-410) can be used.

In another specific embodiment of methods for producing TRACP5b of the present invention, TRACP5b is produced in the silkworm fat body. More specifically, the present invention relates to methods for producing TRACP5b comprising the steps (a) and (b) described below:

(a) producing a silkworm which comprises a promoter of a cytoplasmic actin protein-encoding DNA and a DNA encoding TRACP5 whose expression is regulated directly or indirectly by the promoter, and which secretes TRACP5b into the fat body; and (b) recovering said TRACP5b from the produced silkworm.

In the step of producing silkworms of the present invention, first, silkworm eggs are produced to comprise a promoter of a cytoplasmic actin protein-encoding DNA and a DNA encoding TRACP5 whose expression is regulated directly or indirectly by the promoter. Next, from the silkworms hatched from the produced silkworm eggs, silkworms that secrete TRACP5b into the fat body are selected. Selection of silkworms can be performed by the above-mentioned methods.

In the present invention, silkworm eggs comprising a promoter of a cytoplasmic actin protein-encoding DNA and a DNA encoding TRACP5 whose expression is regulated directly by the promoter are, for example, silkworm eggs comprising a DNA in which a DNA encoding TRACP5 is operably linked downstream of a promoter of a cytoplasmic actin protein-encoding DNA. Such silkworm eggs can be produced by introducing a DNA in which a DNA encoding TRACP5 is operably linked downstream of a promoter of a cytoplasmic actin protein-encoding DNA into silkworm eggs.

Furthermore, in the present invention, silkworm eggs which comprise a promoter of a cytoplasmic actin protein-encoding DNA and a DNA encoding TRACP5 whose expression is regulated indirectly by the promoter are, for example, silkworm eggs comprising (i) a DNA in which a DNA encoding a transcriptional regulator is operably linked downstream of a promoter of a cytoplasmic actin protein-encoding DNA, and (ii) a DNA in which a TRACP5-encoding DNA is operably linked downstream of a target promoter of the transcriptional regulator. The phrase "operably linked" is defined as described above. Examples of combinations of transcriptional regulator and target sequence include those described above.

Silkworm eggs can be produced by the above-mentioned methods. For example, the DNAs of (i) and (ii) described above are introduced into separate silkworm eggs. Silkworm eggs carrying both DNAs can be obtained by crossing silkworms hatched from silkworm eggs into which the respective DNAs have been introduced. Alternatively, silkworm eggs comprising the DNAs of (i) and (ii) can be obtained by artificially introducing one of the DNAs into eggs laid by silkworms introduced with the other DNA. Furthermore, silkworm eggs carrying the DNAs of (i) and (ii) can be obtained by introducing both DNAs into the same eggs. DNAs can be introduced into silkworm eggs by the above-described methods.

Examples of a promoter of a cytoplasmic actin protein-encoding DNA described above include DNAs comprising the nucleotide sequence of SEQ ID NO: 10. Examples of DNAs comprising the nucleotide sequence of SEQ ID NO: 10 include the DNA consisting of the nucleotide sequence of SEQ ID NO: 10, and DNAs that comprise an upstream region or downstream region of the DNA consisting of the nucleotide sequence of SEQ ID NO: 10, but are not limited thereto.

Furthermore, in the present invention, a promoter of a cytoplasmic actin protein-encoding DNA is, for example, a DNA which is structurally similar to a DNA comprising the nucleotide sequence of SEQ ID NO: 10 and has an equivalent or improved promoter activity compared to a DNA comprising the nucleotide sequence of SEQ ID NO: 10. Such promoters can be prepared by the methods described above. The upstream region and downstream region of the DNAs consisting of the nucleotide sequence of SEQ ID NO: 10 are disclosed in MANGE, A., E. JULIEN, J. C. PRUDHOMME and P. COUBLE, 1997 A strong inhibitory element down-regulates SRE-stimulated transcription of the A3 cytoplasmic actin gene of *Bombyx mori*. J. Mol. Biol. 265: 266-274.

The combinations of transcriptional regulator and target sequence described above can be used. A specific embodiment and method for producing a silkworm (a silkworm produced from a silkworm egg having the DNA of (i) described above) whose genome has been inserted with a gene prepared by linking the GAL4 gene downstream of the promoter of a cytoplasmic actin-encoding DNA are disclosed in IMAMURA, M., J. NAKAI, S. INOUE, G. X. QUAN, T. KANDA et al., 2003 Targeted gene expression using the GAL4/UAS system in the silkworm *Bombyx mori*. Genetics 165: 1329-1340.

In the present invention, a DNA encoding a TRACP5 whose expression is regulated directly or indirectly by the promoter of a cytoplasmic actin protein-encoding DNA may comprise a signal sequence. Specific embodiments of the signal sequence are those described above.

TRACP5b produced by the above-mentioned methods can be recovered, for example, from the fat body. TRACP5b can be recovered from the fat body by methods known to those skilled in the art, for example, by removing the fat body from a larval body; and homogenizing it in a buffer for protein extraction, or inducing secretion of proteins from the fat body into the body fluid and then fractionating the body fluid.

In addition, separation of TRACP5b and TRACP5a can be performed by the methods described above.

TRACP5b produced by the methods of the present invention are not particularly limited so long as they are produced by the methods of the present invention, and they may or may not comprise a signal sequence. More specifically, TRACP5b produced by the TRACP5 production methods of the present invention include both TRACP5b comprising a signal sequence and TRACP5b without a signal sequence.

Furthermore, the present invention relates to silkworms which comprise TRACP5-encoding DNA and secrete TRACP5b. More specifically, the present invention relates to silkworms which comprise a promoter of a DNA encoding a protein specifically expressed in the silk gland and a DNA encoding TRACP5 whose expression is regulated directly or indirectly by the promoter, and which secrete TRACP5b into the silk gland. In addition, the present invention provides silkworms which comprise (i) a DNA encoding a transcriptional regulator operably linked downstream of a promoter of a DNA encoding a protein specifically expressed in the silk gland, and (ii) a TRACP5-encoding DNA operably linked downstream of a target promoter of the transcriptional regulator; and silkworms comprising a DNA in which a TRACP5-encoding DNA is operably linked downstream of a promoter of a DNA encoding a protein specifically expressed in the silk gland.

In the present invention, DNAs encoding TRACP5 whose expression is regulated directly or indirectly by a promoter of a DNA encoding a protein specifically expressed in the silk gland preferably comprise signal sequences for promoting TRACP5b secretion and increasing the amount of recovered TRACP5b. Specific embodiments of the signal sequence are those described above.

Furthermore, the present invention relates to silkworms which comprise a promoter of a cytoplasmic actin protein-encoding DNA and a DNA encoding TRACP5 whose expression is regulated directly or indirectly by the promoter, and which secrete TRACP5b into the fat body. More specifically, the present invention provides silkworms comprising (i) a DNA encoding a transcriptional regulator operably linked downstream of a promoter of a cytoplasmic actin protein-encoding DNA, and (ii) a TRACP5-encoding DNA operably linked downstream of a target promoter of the transcriptional regulator; and silkworms comprising a DNA in which a TRACP5-encoding DNA is operably linked downstream of a promoter of a cytoplasmic actin protein-encoding DNA.

In the present invention, DNAs encoding TRACP5 whose expression is regulated directly or indirectly by a promoter of a cytoplasmic actin protein-encoding DNA may comprise a signal sequence for promoting TRACP5b secretion and increasing the amount of recovered TRACP5b. Specific embodiments of the signal sequence are those described above. The silkworms of the present invention also include their eggs.

These silkworms can be produced by the methods described above. Furthermore, there are no particular limitations on the form of the silkworms of the present invention, and for example, they may be in the form of eggs. Large amounts of TRACP5b can be produced by using the silkworms of the present invention.

The present invention also provides silkworms comprising a TRACP5-encoding DNA operably linked downstream of a target promoter of a transcriptional regulator. Examples of transcriptional regulators and target promoters are those mentioned above. Such silkworms can be used to produce silkworms carrying the DNAs of (i) and (ii) described above, and to produce eggs for these silkworms.

In the present invention, DNAs encoding TRACP5 whose expression is regulated directly or indirectly by a promoter of a DNA encoding a protein specifically expressed in the silk gland may comprise a signal sequence for promoting TRACP5b secretion and increasing the amount of recovered TRACP5b. Specific embodiments of the signal sequence are those described above.

Furthermore, the present invention provides cocoons spun by the silkworms of the present invention. Such cocoons are useful as cocoons that contain large amounts of TRACP5b. The present invention also provides silk threads produced from the cocoons and containing TRACP5b. Silk fabrics containing the silk threads of the present invention, for example, silk fabrics containing TRACP5b, can be produced by known methods. The present invention also provides such silk fabrics.

The present invention provides DNAs to be used in the methods of the present invention. Such DNAs include (a) a DNA encoding a transcriptional regulator operably linked downstream of a promoter of a DNA encoding sericin or fibroin, (b) a DNA encoding TRACP5 operably linked downstream of a target promoter of the transcriptional regulator, and (c) a DNA in which a TRACP5-encoding DNA is operably linked downstream of a promoter of a DNA encoding sericin or fibroin; and kits containing combinations of these DNAs can be provided. The present invention also provides vectors in which the DNAs of (a) to (c) are inserted between the inverted terminal repeats of transposons. Furthermore, the present invention provides kits containing the vectors and vectors comprising transposase-encoding DNAs (helper vectors).

TRACP5-encoding DNAs operably linked downstream of a target promoter of a transcriptional regulator, and DNAs in which a TRACP5-encoding DNA is operably linked downstream of a promoter of a sericin- or fibroin-encoding DNA, may comprise a signal sequence for promoting TRACP5b secretion and increasing the amount of recovered TRACP5b. Specific embodiments of the signal sequence are those described above.

TRACP5b obtained by the production method of the present invention can be used, for example, in screening for candidate compounds for TRACP5b-specific inhibitors, activators, or modulators. TRACP5b-specific inhibitors, activators, or modulators are useful for treating diseases associated with increased bone resorption. Diseases associated with increased bone resorption include tissue disorders, metabolic bone diseases, osteoporosis, and such, but are not limited thereto.

Screening for a candidate compound for TRACP5b-specific inhibitor, activator, or modulator can be carried out, for example, by a method comprising steps (a) to (c) below:

(a) mixing a test compound with TRACP5b produced by the method of the present invention, in the presence of a substrate for TRACP5b;

(b) measuring TRACP5b activity; and (c) selecting the test compound that alters the TRACP5b activity as compared to the activity in the absence of the test compound.

In the screening for a candidate compound for a TRACP5b-specific inhibitor, activator, or modulator, a test compound and TRACP5b produced by the method of the present invention are initially mixed in the presence of a substrate for TRACP5b. The test compound in the method of the present invention is not particularly limited, and includes, for example, single compounds such as naturally-occurring compounds, organic compounds, inorganic compounds, proteins, or peptides, as well as compound libraries, expression products of gene libraries, cell extracts, cell culture supernatants, microbial fermentation products, marine organism extracts, plant extracts, prokaryotic cell extracts, eukaryotic single cell extracts, or animal cell extracts.

The substrate for TRACP5b includes synthetic substrates such as p-nitrophenyl phosphate ester, but is not limited thereto.

TRACP5b activity is assayed, for example, by using p-nitrophenyl phosphate ester as a substrate and measuring the amount of the hydroxy compound, i.e. p-nitrophenol, produced by the reaction between TRACP5b and the substrate. The amount of p-nitrophenol can be measured, for example, by measuring the absorbance at a wavelength of 405 nm, and the TRACP5b activity can be assayed by measuring a change in absorbance at that wavelength.

Finally, the TRACP5b activity assayed above is compared to the TRACP5b activity assayed in the absence of the test compound. As a result of the comparison, the test compound that changes the TRACP5b activity will be selected as a TRACP5b modulator. In particular, the test compound that decreases the TRACP5b activity will be selected as a candidate compound for a TRACP5b-specific inhibitor. Furthermore, the test compound that increases the TRACP5b activity as a result of the comparison will be selected as a candidate compound for a TRACP5b activator.

All prior art references cited in this specification are incorporated herein by reference.

Examples

Herein below, the present invention will be specifically described with reference to Examples, but it is not to be construed as being limited thereto.

Materials and Methods

[Vector Construction]

In the present invention, first, the plasmid vector pBMCSUASsigTRACP (FIG. 1 and SEQ ID NO: 1) to be used for expressing human TRACP in transgenic silkworms was produced. This vector for production of transgenic silkworms has a human TRACP gene that is inserted between the inverted terminal repeats of the piggyBac transposon, and located downstream of the promoter UAS, which promotes gene expression in the presence of a yeast transcriptional regulator, GAL4. Furthermore, this vector carries the green fluorescent protein gene 3×P3GFP as a marker gene to identify transgenic silkworms, which is linked to a promoter that promotes expression in the stemmata of embryos, compound eyes of moths, and nerve-derived tissues (Horn, C., and E. A. Wimmer, (2000) Dev. Genes Evol. 210: 630-637; Murizio et al. (1994) Protein Science, 3: 1476-1484).

[Production of Transgenic Silkworms and Establishment of Recombinant Protein-Expressing Strains]

Figure 2:
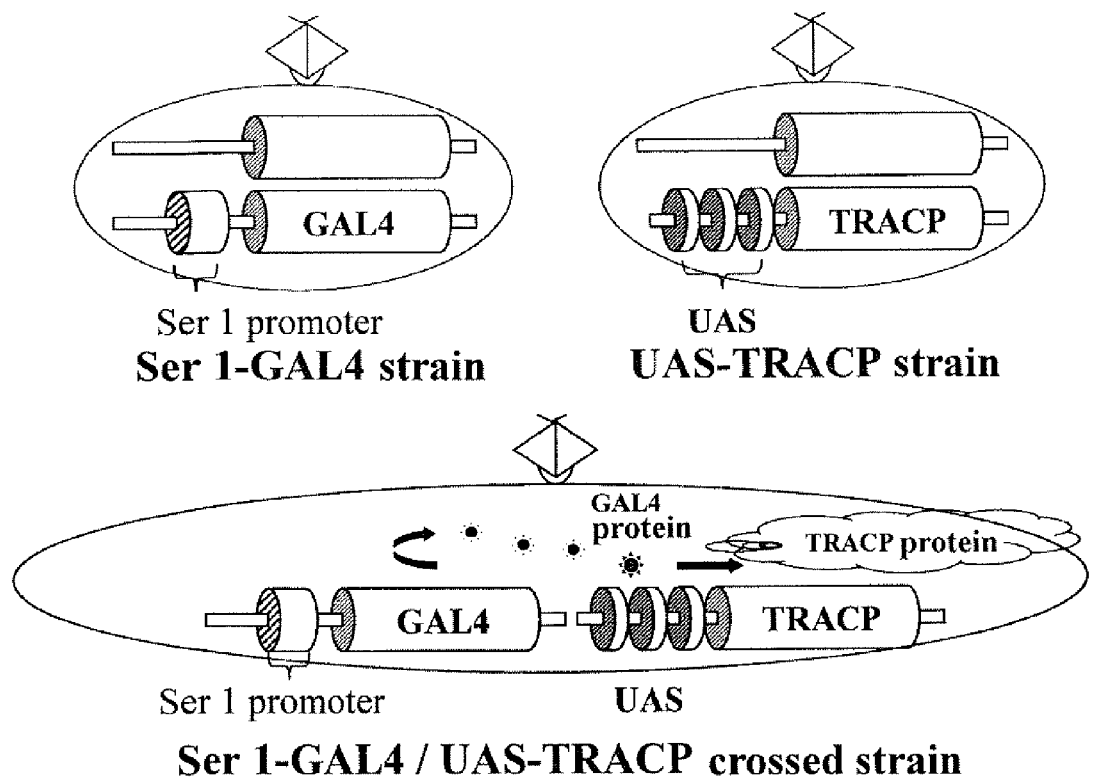
FIG. 2 illustrates establishment of human TRACP-expressing silkworms by crossing the Ser1-GAL4 strain with the UAS-TRACP strain.
Figure 3:
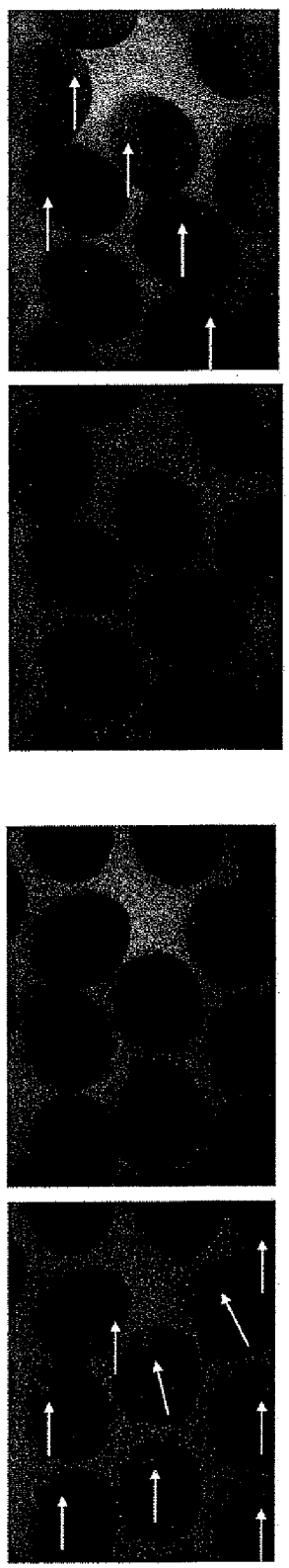
FIG. 3 shows fluorescence stereo micrographs of silkworm is carrying the GAL4 gene and individuals carrying UAS.
Figure 3:
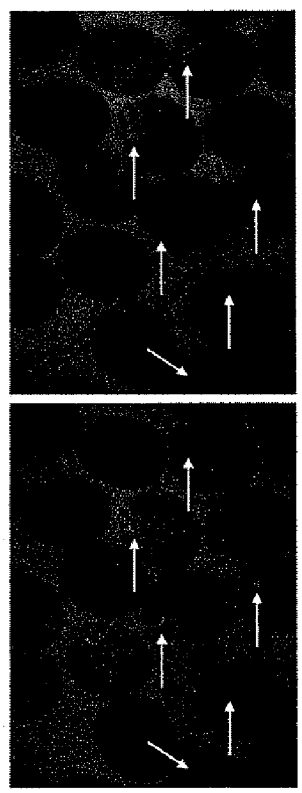

For the production of transgenic silkworms, the plasmid vector pBMCSUASsigTRACP and a helper plasmid were injected into 461 early silkworm embryos. Early embryos carrying the marker gene from 60 examined moth eggs were examined, and five broods of transgenic silkworms were identified (Table 1). From among them, three broods of transgenic silkworms were finally established as strains. In the present invention, the already established Ser1-GAL4 strain (Tamura et al., Abstracts of the 74th Meeting of the Japanese Society of Sericultural Science, p. 51) was used as the GAL4 strain to express the human tartrate-resistant acid phosphatase gene in the silk gland. This transgenic silkworm expresses a red fluorescent protein in the stemmata of embryos and compound eyes of moths. Furthermore, this transgenic silkworm has been found to express a transgene regulated by UAS since the GAL4 gene is expressed only in the middle silk gland (Tamura et al., 2004). To express the introduced human TRACP gene, two strains out of the obtained three UAS-TRACP strains were crossed with the above-mentioned Ser1-GAL4 strain, as shown in FIG. 2. In the Ser1-GAL4 strain used herein, the red fluorescent protein is expressed in the stemmata of the embryos. Eggs of the next generation obtained by crossing the UAS-TRACP strains with the Ser1-GAL4 strain were observed 6 days after oviposition under a fluorescence stereomicroscope to identify Ser1-GAL4/UAS-TRACP individuals carrying both the red fluorescent protein and the green fluorescent protein (FIG. 3). The Ser1-GAL4/UAS-TRACP individuals were raised, the silk gland was removed from 5th instar spinning silkworms, and proteins were extracted using 20 mM Tris-HCl/100 mM NaCl at pH 7.4. Similarly, as a control, the silk gland was removed on day 0 of spinning from the 5th instar Ser1-GAL4 strain silkworms which did not have the human TRACP gene, and proteins were extracted.

TABLE 1

| Vector | Number of injected eggs | Number of hatched eggs | Number of moth eggs examined | Number of transgenic moth broods |
|---|---|---|---|---|
| pBMCSUASsigTRACP | 461 | 185 | 60 | 5 |

[RT-PCR]

RT-PCR was performed as follows to confirm the transcription of human TRACP gene. As described above, individuals having both GAL4 and UAS genes were raised, and the middle silk gland was removed from 5th instar spinning silkworms. Similarly, as a control, the silk gland was removed on day 0 of spinning from 5th instar Ser1-GAL4 strain silkworms. Next, the removed middle silk glands were transferred to a glass homogenizer (WHEATON), and total RNAs were extracted using ISOGEN (Nippon Gene). The total RNAs were adjusted to 50 g/20 μL with DEPC water, and then reverse transcribed into cDNAs using a First-strand cDNA Synthesis Kit (GE Healthcare) according to the attached document. PCR was performed as follows using the reverse transcripts as a template. Specifically, 5 μL of 10×PCR buffer attached to TaKaRa Ex Taq HS (Takara Bio Inc.), 150 μM of the plasmid vector pBMCSUASsigTRACP (SEQ ID NO: 1), 150 μM each of the primers (SEQ ID NOs: 2 and 3), and 0.2 mM dNTPs were mixed to give 2 units of EX Taq HS, and the total volume was adjusted to 50 μL. PCR was carried out using an Eppendorf DNA thermal cycler with one cycle of 98° C. for 2 minutes; 40 cycles of 98° C. for 10 seconds, 57.5° C. for 30 seconds, and 72° C. for 30 seconds; and one cycle of 72° C. for 4 minutes for elongation.

[Activity Assay]

TRACP5b was assayed in the following manner. The protein solution extracted from the silk gland of Ser1-Gal4/UAS-TRACP individuals or the control Ser1-GAL4 individuals was applied to a microplate sensitized with the human TRACP5b-recognizing monoclonal antibody Trk62 (IPOD Accession No. FERMBP7890), and reacted at room temperature for one hour. After a subsequent washing operation, a substrate buffer containing tartaric acid and chloronitrophenyl phosphate was added, and incubated at 37° C. for one hour, and the 405-nm absorbance was measured to assay TRACP5b (Table 2).

[Confirmation of TRACP5b Production by Acidic Disc Electrophoresis]

Figure 5:
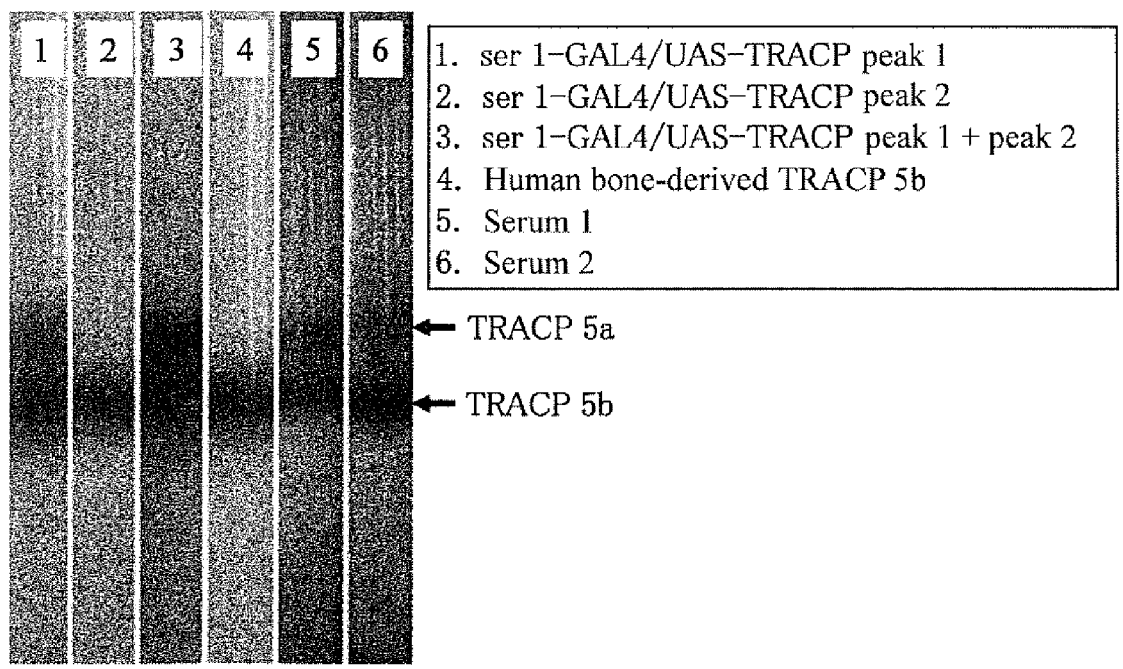
FIG. 5 shows the activity staining carried out in the acidic disc electrophoresis, which demonstrates the production of TRACP5b because TRACP obtained from TRACP-expressing silkworms showed a band in the bottom cathode side as in the human bone-derived TRACP or serum TRACP.

Acidic disc electrophoresis was performed by the following procedure. A 45-mm layer of 7.5% acrylamide separating gel was applied to the glass capillary tube of a disc electrophoresis apparatus (ATTO), and 4 mm of 2.5% acrylamide concentrating gel was layered over it. The protein solution extracted from the silk gland of the Ser1-GAL4/UAS-TRACP individuals, namely silkworms of the present invention, was applied to a CM-Sepharose column, and eluted using 10 mM Tris-HCl pH 7.2 with a linear gradient of 0-0.5 M NaCl. TRACP activity of the eluted fractions was measured, and fractions with TRACP activity were collected and concentrated using a spin column. Subsequently, gel filtration was carried out using a Superdex200 column, and fractions having TRACP activity were similarly collected and concentrated. Furthermore, the fractions having TRACP activity were purified using a heparin column (HiTrap Heparin HP, GE Healthcare) and a linear gradient (0.35 M 1 M) of NaCl in 20 mM Tris-HCl, pH 7.2. Fractions containing peak 1 and peak 2, which had TRACP activity, were each concentrated to 20 U/L using a spin column. BSA and glycerol were added to 50 µL of these concentrated samples, and then applied to the top of the capillary tube. Then, using an electrophoresis buffer of 35 mM β-alanine pH 4.0, electric current was applied at 4 mA/capillary for 90 minutes such that the anode was at the top of the capillary. After current application was completed, activity staining was carried out by soaking the gel in a staining solution of 0.1 M citric acid buffer (pH 5.0) containing α-naphthylic acid, Fast Garnet GBC, and tartaric acid. The same electrophoresis was also performed on a human serum as a control. As a result, as shown in FIG. 5, the recombinant protein extracted from the Ser1-GAL4/UAS-TRACP individuals clearly indicated the production of TRACP5b, as in human bone-derived TRACP5b or human serum.

Results

Figure 4:
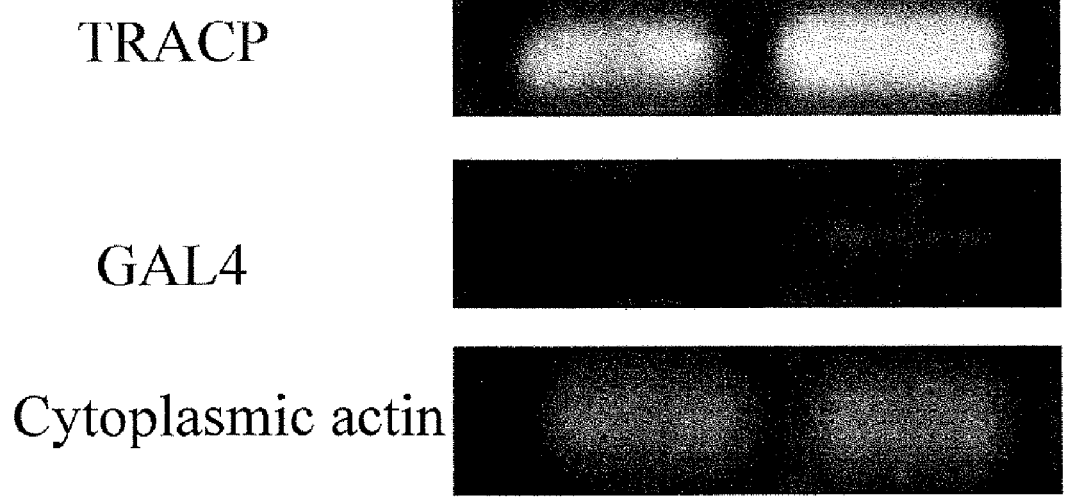
FIG. 4 is a photograph showing confirmation of the transcription of GAL4 and TRACP genes in the hybrid strain by RT-PCR.

FIG. 1 shows a plasmid vector for producing silkworms transgenic for the human tartrate-resistant acid phosphatase gene. This plasmid vector and the helper plasmid pA3PIG (Tamura et al., Nature Biotechnology (2000) 18, 81-84.) were injected into 461 silkworm eggs. As a result of observing the green fluorescent protein expressed in the stemmata of embryos of the next generation under a fluorescence stereomicroscope, five transgenic moth broods were identified (Table 1). These transgenic silkworms were raised, and three moth broods were established as strains. As shown in FIG. 2, the obtained UAS-TRACP strains were crossed with the Ser1-GAL4 strain to establish the Ser1-GAL4/UAS-TRACP strains expressing the recombinant human tartrate-resistant acid phosphatase. Embryos were observed under a fluorescence stereomicroscope 6 days after oviposition by the female moths crossed as above, and those carrying both the red fluorescent protein and the green fluorescent protein in the stemmata were identified as shown in FIG. 3. The Ser1-GAL4/UAS-TRACP strain was raised, and total RNAs were extracted from the silk gland at the 5th instar spinning stage. RT-PCR of the obtained total RNAs confirmed the transcription of the GAL4 gene and TRACP gene as shown in FIG. 4.

TRACP5b was present in the proteins derived from the silk glands of the two Ser1-GAL4/UAS-TRACP strains, but not in the control. In addition, the acidic electrophoresis in which the anode was the top of the capillary also showed that TRACP5b could be obtained from the solutions extracted from the silk gland of the silkworms of the present invention.

TABLE 2

|  | Human TRACP5b activity (U/L) |
|---|---|
| ser1-GAL4/UAS-TRACP 01 | 17.6 |
| ser1-GAL4/UAS-TRACP 02 | 8.9 |
| Control | 0.0 |

INDUSTRIAL APPLICABILITY

The present invention provides methods for producing TRACP5b using silkworms. Conventionally, in order to obtain TRACP5b, it had to be extracted from human bones that became unnecessary due to some reason such as injury. However, this method only yields a small amount of TRACP5b. On the other hand, by using the present invention, TRACP5b can be produced in large amounts as shown below.

First, silkworms for producing TRACP5b have organs called silk glands, which are suitable for producing proteins, and are capable of producing several hundred milligrams of protein per animal. Furthermore, silkworms can be reared under clean conditions using an artificial diet, and large-scale rearing at the level of several tens of thousands of silkworms can be easily carried out. In addition, since large-scale rearing of silkworms can be carried out using mulberry leaves abundant in nature, TRACP5b can be produced at a low cost.

TRACP5b obtained by the methods of the present invention can be used, for example, to screen for candidate compounds for TRACP5b-specific inhibitors, activators, or modulators.

The invention claimed is:

1. A method for producing TRACP5b, wherein the method comprises the steps of:
   (a) producing a silkworm which comprises a promoter of a DNA encoding a protein specifically expressed in its silk gland operably linked to a DNA encoding tartrate-resistant acid phosphatase-5 (TRACP5) comprising a signal sequence, and which secretes TRACP5b into the silk gland; and
   (b) recovering said TRACP5b from the produced silkworm.

2. The method of claim 1, wherein the silkworm comprises the DNAs of (i) and (ii):
   (i) a DNA encoding a transcriptional regulator, which is operably linked downstream of a promoter of a DNA encoding a protein specifically expressed in the silk gland; and
   (ii) a DNA encoding TRACP5, which is operably linked downstream of a target promoter of the transcriptional regulator.

3. The method of claim 1, wherein the silkworm is produced by crossing the silkworms of (i) and (ii):
   (i) a silkworm comprising a DNA encoding a transcriptional regulator, which is operably linked downstream of a promoter of a DNA encoding a protein specifically expressed in the silk gland; and
   (ii) a silkworm comprising a DNA encoding TRACP5, which is operably linked downstream of a target promoter of the transcriptional regulator.

4. The method of claim 3, wherein the transcriptional regulator is GAL4 and the target promoter is UAS.

5. The method of claim 1, wherein the silk gland is middle silk gland or posterior silk gland.

6. The method of claim 5, wherein the promoter of a DNA encoding a protein specifically expressed in the silk gland is a promoter of a DNA encoding a sericin 1 protein or sericin 2 protein.

7. The method of claim 5, wherein the promoter of a DNA encoding a protein specifically expressed in the silk gland is a promoter of a DNA encoding a fibroin protein.

8. A method for producing a silkworm that secretes tartrate-resistant acid phosphatase-5b (TRACP5b), which comprises the step of introducing a DNA sequence encoding TRACP5 comprising a signal sequence operably linked to a promoter of a DNA encoding a protein specifically expressed in its silk gland into a silkworm egg.

9. A method for producing a silkworm that secretes tartrate-resistant acid phosphatase-5b (TRACP5b) into its silk gland, which comprises the step of producing a silkworm egg which comprises a promoter of a DNA encoding a protein specifically expressed in the silk gland operably linked to a DNA encoding TRACP5 comprising a signal sequence.

10. The method of claim 9, wherein the silkworm comprises the DNAs of (i) and (ii):
   (i) a DNA encoding a transcriptional regulator, which is operably linked downstream of a promoter of a DNA encoding a protein specifically expressed in the silk gland; and
   (ii) a DNA encoding TRACP5, which is operably linked downstream of a target promoter of the transcriptional regulator.

11. The method of claim 9, wherein the silkworm is produced by crossing the silkworms of (i) and (ii):

(i) a silkworm comprising a DNA encoding a transcriptional regulator, which is operably linked downstream of a promoter of a DNA encoding a protein that is specifically expressed in the silk gland; and (ii) a silkworm comprising a DNA encoding TRACP5, which is operably linked downstream of a target promoter of the transcriptional regulator.

12. The method of claim 10 or 11, wherein the transcriptional regulator is GAL4 and the target promoter is UAS.

13. The method of claim 9, wherein the silk gland is middle silk gland or posterior silk gland.

14. The method of claim 13, wherein the promoter of a DNA encoding a protein that is specifically expressed in the silk gland is a promoter of a DNA encoding a sericin 1 protein or sericin 2 protein.

15. The method of claim 13, wherein the promoter of a DNA encoding a protein that is specifically expressed in the silk gland is a promoter of a DNA encoding a fibroin protein.

16. A silkworm which comprises a promoter of a DNA encoding a protein that is specifically expressed in its silk gland operably linked to a DNA sequence encoding tartrate-resistant acid phosphatase-5 (TRACP5) comprising a signal sequence, and which secretes TRACP5b into the silk gland.

17. The silkworm of claim 16, which comprises the DNAs of (i) and (ii):

(i) a DNA encoding a transcriptional regulator, which is operably linked downstream of a promoter of a DNA encoding a protein specifically expressed in the silk gland; and (ii) a DNA encoding TRACP5, which is operably linked downstream of a target promoter of the transcriptional regulator.

18. The silkworm of claim 16, which is produced by crossing the silkworms of (i) and (ii):

(i) a silkworm comprising a DNA encoding a transcriptional regulator, which is operably linked downstream of a promoter of a DNA encoding a protein that is specifically expressed in the silk gland; and (ii) a silkworm comprising a DNA encoding TRACP5, which is operably linked downstream of a target promoter of the transcriptional regulator.

19. The silkworm of claim 17 or 18, wherein the transcriptional regulator is GAL4 and the target promoter is UAS.

20. The silkworm of claim 16, wherein the silk gland is middle silk gland or posterior silk gland.

21. The silkworm of claim 20, wherein the promoter of a DNA encoding a protein that is specifically expressed in the silk gland is a promoter of a DNA encoding a sericin 1 protein or sericin 2 protein.

22. The silkworm of claim 20, wherein the promoter of a DNA encoding a protein that is specifically expressed in the silk gland is a promoter of a DNA encoding a fibroin protein.

* * * * *

UNITED STATES PATENT AND TRADEMARK OFFICE
CERTIFICATE OF CORRECTION

PATENT NO. : 8,426,674 B2
APPLICATION NO. : 12/521701
DATED : April 23, 2013
INVENTOR(S) : Kiyokawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 648 days.

Signed and Sealed this
Eighth Day of September, 2015

Michelle K. Lee
*Director of the United States Patent and Trademark Office*